(12) United States Patent
Smith

(10) Patent No.: US 11,399,918 B2
(45) Date of Patent: Aug. 2, 2022

(54) ORTHODONTIC DEVICE

(71) Applicant: Nicholas Smith, Austin, TX (US)

(72) Inventor: Nicholas Smith, Austin, TX (US)

( * ) Notice: Subject to any disclaimer, the term of this patent is extended or adjusted under 35 U.S.C. 154(b) by 247 days.

(21) Appl. No.: 16/504,269

(22) Filed: Jul. 7, 2019

(65) Prior Publication Data

US 2019/0336249 A1  Nov. 7, 2019

(51) Int. Cl.
*A61C 7/14* (2006.01)
*A61C 7/20* (2006.01)
*C01B 32/158* (2017.01)
*A61C 7/28* (2006.01)

(52) U.S. Cl.
CPC ............... *A61C 7/148* (2013.01); *A61C 7/20* (2013.01); *A61C 7/28* (2013.01); *C01B 32/158* (2017.08); *A61L 2400/12* (2013.01)

(58) Field of Classification Search
CPC .. A61C 7/00; A61C 7/148; A61C 7/16; A61C 7/20; A61C 7/28; A61C 7/282; A61C 7/30; A61C 7/12; C01B 32/158; A61L 2400/12
USPC ................................................. 433/9, 20, 22
See application file for complete search history.

(56) References Cited

U.S. PATENT DOCUMENTS

| | | | | |
|---|---|---|---|---|
| 10,278,791 | B2* | 5/2019 | Schumacher | ............ A61C 7/08 |
| 2006/0204738 | A1* | 9/2006 | Dubrow | .................. A61L 27/34 |
| | | | | 428/292.1 |
| 2007/0106363 | A1* | 5/2007 | Weber | ................... A61L 31/084 |
| | | | | 623/1.11 |
| 2011/0311932 | A1* | 12/2011 | Parker | ...................... A61C 7/12 |
| | | | | 433/9 |
| 2014/0154637 | A1* | 6/2014 | Hansen | .................... A61C 7/20 |
| | | | | 433/20 |
| 2016/0325010 | A1* | 11/2016 | Liebler | ............... A61L 26/0023 |

* cited by examiner

*Primary Examiner* — Heidi M Eide
*Assistant Examiner* — Drew S Folgmann
(74) *Attorney, Agent, or Firm* — Michael G. Smith, Esq.

(57) ABSTRACT

Systems, methods and apparatus are provided through which in some implementations an orthodontic apparatus includes a plurality of brackets, wherein each of the plurality of brackets includes a carbon-nanotube forest upon a carbon-nanotube bonding substrate that is adhered to a lingual bracket bonding surface, forming a plurality of carbon-nanotube bonding substrates.

1 Claim, 29 Drawing Sheets

2100

|  | Archwire 1 | Archwire 2 | Archwire 3 | Archwire 4 | Archwire 5 |
|---|---|---|---|---|---|
| ML-1 | 7.4 mm | 8.5 mm | 9.5 mm | 10.6 mm | 11.6 mm |
| Space 1-2 | 6.4 mm | 7.6 mm | 8.7 mm | 9.8 mm | 11.0 mm |
| Space 2-3 | 5.8 mm | 7.0 mm | 8.3 mm | 9.5 mm | 10.8 mm |
| Space 3-4 | 6.0 mm | 7.3 mm | 8.5 mm | 9.7 mm | 11.0 mm |
| Space 4-5 | 5.5 mm | 6.8 mm | 7.8 mm | 9.0 mm | 10.0 mm |
| Space 5-6 | 6.7 mm | 7.8 mm | 9.0 mm | 10.0 mm | 11.0 mm |
| Space 6-7 | 7.6 mm | 8.9 mm | 10.0 mm | 11.0 mm | 12.2 mm |

UPPER ARCHWIRE TOOTH-BONDING-PAD
SPACING

|  | Archwire 1 | Archwire 2 | Archwire 3 | Archwire 4 | Archwire 5 |
|---|---|---|---|---|---|
| ML-1 | 4.2 mm | 5.0 mm | 5.6 mm | 6.6 mm | 7.5 mm |
| Space 1-2 | 4.4 mm | 5.2 mm | 6.0 mm | 7.0 mm | 8.0 mm |
| Space 2-3 | 5.2 mm | 6.0 mm | 6.7 mm | 8.0 mm | 9.0 mm |
| Space 3-4 | 5.8 mm | 6.8 mm | 7.4 mm | 8.5 mm | 9.6 mm |
| Space 4-5 | 6.0 mm | 7.0 mm | 7.4 mm | 8.5 mm | 9.5 mm |
| Space 5-6 | 7.4 mm | 8.4 mm | 9.2 mm | 10.2 mm | 11.2 mm |
| Space 6-7 | 8.7 mm | 9.7 mm | 10.6 mm | 11.6 mm | 12.5 mm |

LOWER ARCHWIRE TOOTH-BONDING-PAD
SPACING

FIG. 22

ORTHODONTIC DEVICE

FIELD

This disclosure relates generally to orthodontic devices, and more particularly to orthodontic archwire devices.

BACKGROUND

An orthodontic archwire is ligated to a number of orthodontic brackets, each of which has a carbon-nanotube bonding substrate as a part of a bracket. An orthodontic archwire is a wire conforming to the alveolar or dental arch that can be used with dental tooth-bonding pads and brackets as a source of force in correcting irregularities in the position of the teeth. The dental tooth-bonding pads are attached to the brackets and the brackets are attached to the archwire. The archwire is attached to the brackets by an orthodontist in the mouth of a patient.

BRIEF DESCRIPTION OF THE DRAWINGS

FIG. 21 is a table of spacing between carbon-nanotube bonding substrates in an upper archwire for a human, according to an implementation.

FIG. 22 is a table of spacing between carbon-nanotube bonding substrates in a lower archwire for a human, according to an implementation.

DETAILED DESCRIPTION

Figure 1:
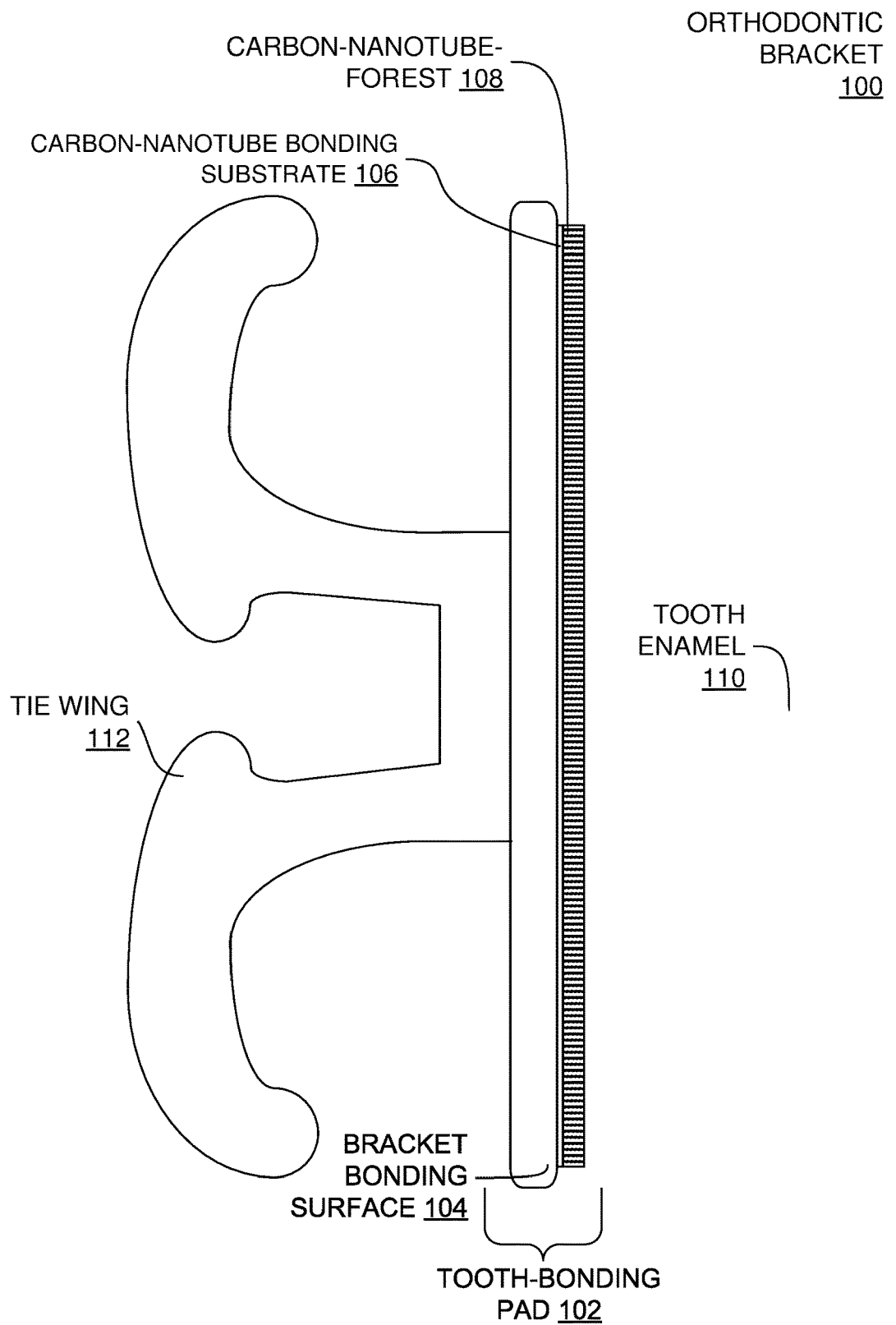
FIG. 1 is a block diagram of an orthodontic bracket having a carbon-nanotube bonding substrate.

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, physical and other changes may be made without departing from the scope of the implementations. The following detailed description is, therefore, not to be taken in a limiting sense.

In one aspect, at least one carbon-nanotube bonding substrate is directly attached to an archwire.

In one other aspect, an apparatus consists of an archwire and a plurality of carbon-nanotube bonding substrates. In some implementations, each of the plurality of carbon-nanotube bonding substrates is permanently fabricated to the archwire at fixed positions of the archwire. In some implementations, each of the plurality of carbon-nanotube bonding substrates is permanently fabricated into the archwire at fixed positions of the archwire. In some implementations, each of the plurality of carbon-nanotube bonding substrates is permanently fabricated onto the archwire at fixed positions of the archwire.

In another aspect, an apparatus consists essentially of an archwire and a plurality of carbon-nanotube bonding substrates. In some implementations, each of the plurality of carbon-nanotube bonding substrates is permanently fabricated into the archwire at fixed positions of the archwire.

In yet another aspect, an apparatus includes an archwire and a plurality of carbon-nanotube bonding substrates. In some implementations, each of the plurality of carbon-nanotube bonding substrates is permanently fabricated into the archwire at fixed positions of the archwire.

In still yet another aspect, an apparatus consists of an archwire and at least one carbon-nanotube bonding substrate directly attached to the archwire.

In still yet a further aspect, an apparatus consists essentially of an archwire and at least one carbon-nanotube bonding substrate directly attached to the archwire.

In still a further aspect, an apparatus comprises an archwire and at least one carbon-nanotube bonding substrate directly attached to the archwire.

In still another aspect, a method includes setting typodont teeth in orthodontically correct positions, placing a plurality of carbon-nanotube bonding substrates onto the typodont teeth in the occlusal-gingival center and mesial-distal center of the labial and buccal aspect of orthodontically correct positions, and attaching permanently an archwire to the exterior surface of each of the plurality of the carbon-nanotube bonding substrates in a plane.

In a further aspect, a method includes setting typodont teeth in orthodontically correct positions, placing a plurality of carbon-nanotube bonding substrates onto the typodont teeth in the occlusal-gingival center and mesial-distal center of the labial and buccal aspect of orthodontically correct positions, and forming an archwire to an exterior surface of each of the plurality of the carbon-nanotube bonding substrates in a horizontal plane.

In yet a further aspect, an orthodontic apparatus having an archwire and at least one carbon-nanotube bonding substrate does not include an orthodontic bracket.

Apparatus, systems, and methods of varying scope are described herein. In addition to the aspects and advantages described herein, further aspects and advantages will become apparent by reference to the drawings and by reading the detailed description that follows.

The detailed description is divided into four sections. In the first section, a system level overview is described. In the second section, apparatus of implementations are described. In the third section, implementations of methods are described. Finally, in the fourth section, a conclusion of the detailed description is provided.

System Level Overview

A system level overview of the operation of an implementation is described in this section of the detailed description.

FIG. 1 is a block diagram of an orthodontic bracket 100 having a carbon-nanotube bonding substrate. An orthodontic bracket 100 includes a tooth-bonding pad 102. The tooth-bonding pad 102 including a bracket bonding surface 104 with a flat surface. The flat surface of the bracket bonding surface 104, which is different than the typical contoured wire mesh bonding surface, allows the attachment of a carbon-nanotube bonding substrate 106. The carbon-nanotube bonding substrate 106 is typically a silicone dioxide growth substrate, however the substrate can be comprised of any substance that promotes carbon-nanotube growth. The carbon-nanotube bonding substrate 106 is the substrate on which the carbon-nanotube forest 108 is grown on through Chemical Vapor Deposition (CVD). The carbon-nanotube bonding substrate 106 is pre-coated with iron metal catalyst particles prior to CVD. During CVD, both Hydrogen gas (process gas) and Acetylene gas (carbon rich gas) are fed into the reaction chamber which triggers decomposition on the heated substrate, growing carbon-nanotubes (CNT)s through precipitation on the iron metal catalyst particles. The inclusion of the Silicone Dioxide Growth Substrate allows for easier manufacturing and a more controlled carbon-nanotube growth process. For example, if the orthodontic bracket 100 was used as the substrate on which the carbon-nanotubes were grown on, there could be carbon-nanotubes that grow on surfaces other than the bracket bonding surface 104. The carbon-nanotube forest 108 allows the bracket bonding surface 104, on the orthodontic bracket 100, to adhere to a tooth enamel 110 through Van der Wall intermolecular forces between the carbon-nanotubes forest 108 and the tooth enamel 110. Additionally, the carbon-nanotube forest 108 allows the installation and removal of the orthodontic bracket 100 from the tooth enamel 110 without the need for dental cement. In addition, tie wing 112 is attached to the bracket bonding surface 104.

Figure 2:
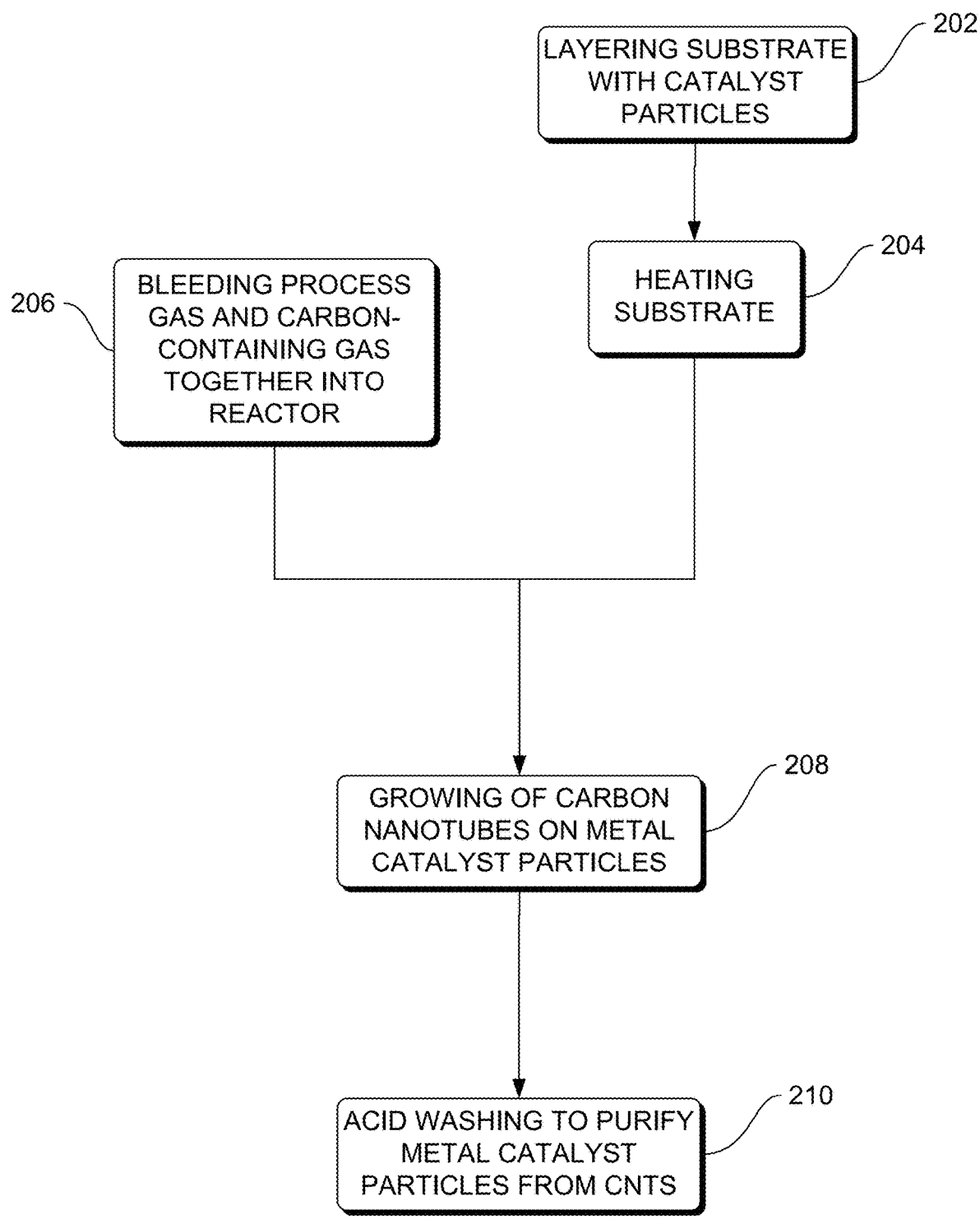
FIG. 2 is a block diagram of a process of manufacturing an orthodontic bracket having a carbon-nanotube bonding substrate.

FIG. 2 is a block diagram of a process 200 of manufacturing an orthodontic bracket having a carbon-nanotube bonding substrate. In the process 200, a substrate, typically silicon, quartz or stainless steel, is coated with a 1-5 nm diameter layer of metal catalyst, typically Iron, Cobalt, or Nickel, via rf-sputtering, at block 202. Catalyst particle diameter determines the size of the carbon-nanotube. The diameter of the metal catalyst particle can also determine the amount of walls contained in the carbon-nanotube. smaller diameters 1-2 nm usually grow single walled carbon-nanotubes, while larger diameters grow multi-walled carbon-nanotubes. Standard rf-sputtering allows for precise amounts of catalyst to be applied to the oxidized silicon substrate. After heating the substrate to 700 Celsius the layer of metal catalyst breaks into small particles which form the "foundation" on which the carbon-nanotubes will grow, at block 204. Heating the substrate provides the energy for the decomposition reaction to take place at the area of the metal catalyst particles which are on the substrate. The diameter of the original layer of metal catalyst determines the size of these metal catalyst particle "foundations", which, in turn, determines the diameters of the carbon-nanotubes. Next, a process gas, such as ammonia, nitrogen, or hydrogen, and a carbon-rich gas, such as acetylene, ethylene, ethanol, or methane, are bled into the reactor, at block 206. The process gas, or reducing gas, is important to add because hydrogen reduces metal catalyst particles. The hydrogen gas flow keeps the metal catalyst particles active by reducing the metal catalyst during the decomposition reaction. The hydrogen gas also reduces the formation of undesirable carbon deposits from the pyrolysis of the carbon gas. The reason hydrogen gas is beneficial in preventing undesirable carbon deposits because the hydrogen gas rehydrogenates the reactive carbon species in the gas phase. The carbon-rich gas is broken down at the sites of the metal catalyst particles and the carbon is transported to the edges of the metal catalyst particles, growing the carbon-nanotubes on the sites of the metal catalyst particles, at block 208. The mechanism of growth at block 208 is through catalytic decomposition of the carbon gas and bulk diffusion of carbon. The carbon-rich gas decomposes at the site of the metal catalyst particle due to the heat of the substrate. The decomposition of the carbon gas provides a carbon rich environment around the heated substrate and metal catalyst. The carbon is absorbed into the metal catalyst particles and precipitates along the edges of the metal catalyst particle. The precipitation is believed to be caused by a temperature gradient that exists on the metal catalyst particles, carbon is not as soluble on the cooler edges (because carbon solubility in metals is temperature dependent) so the excess is precipitates out of the metal catalyst particle. The precipitation causes the "growing" action of the carbon-nanotubes, which continues until the metal catalyst particle is deactivated, which is typically due to carbon formation around the metal catalyst preventing additional carbon-rich gas from reaching the metal catalyst particle. The carbon-nanotubes are then purified from the metal catalyst through an acid wash, at block 210. Carbon-nanotube synthesis leaves a lot of impurities in the way of amorphous carbon molecules and metal catalyst particles. Both of these can affect the properties of the carbon-nanotubes, such as adhesion, so their removal is important. The acid wash dissolves the metal catalyst particles via hydrochloric acid HCl or nitric acid HNO3 and hydrogen peroxide $H_2O_2$ oxidizes the amorphous carbon molecules.

Figure 3:
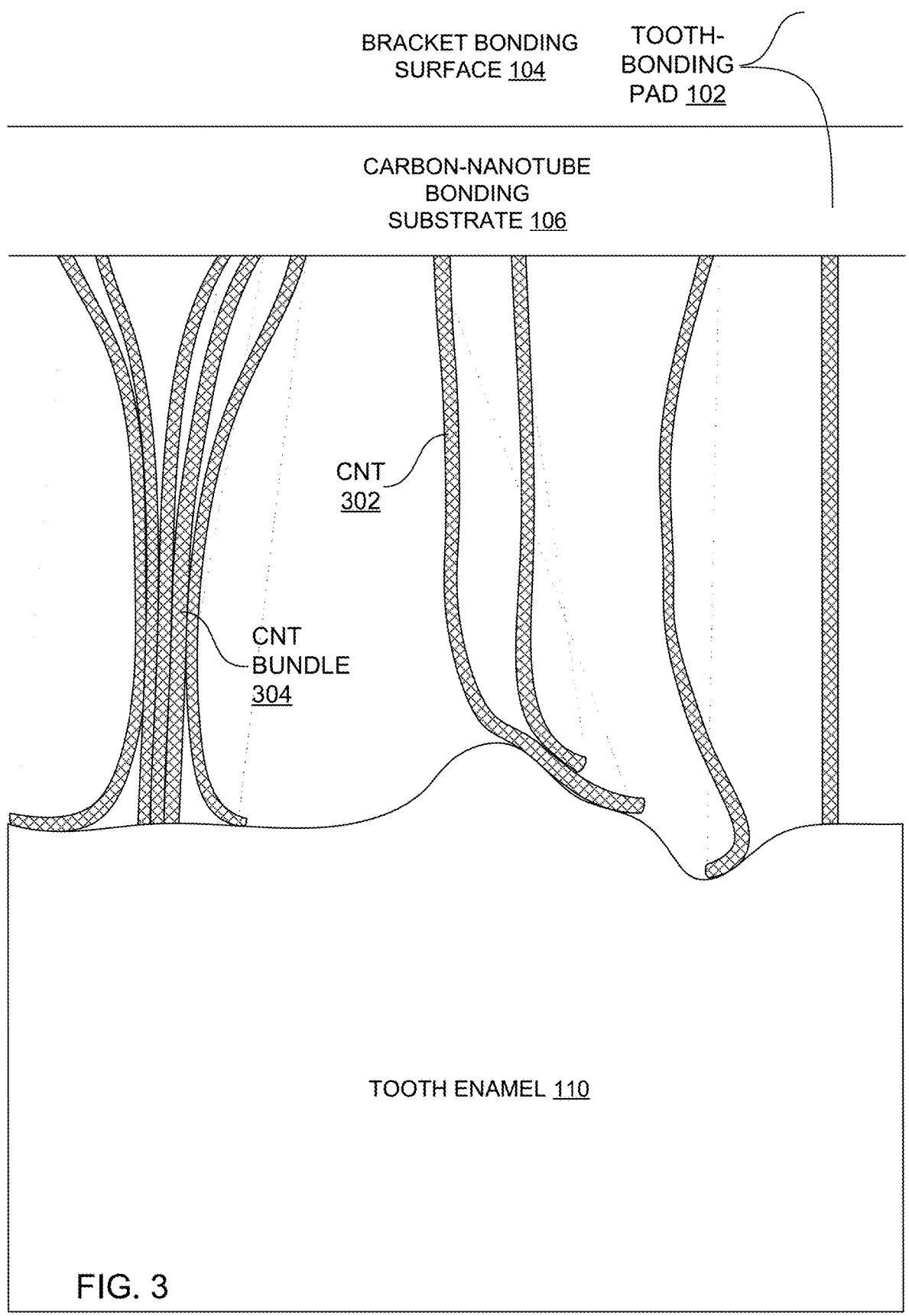
FIG. 3 is a block diagram of an orthodontic bracket having a carbon-nanotube bonding substrate attached to tooth enamel.

FIG. 3 is a block diagram of an orthodontic bracket having a carbon-nanotube bonding substrate 106 of the bracket bonding surface 104 and the tooth-bonding pad 104 attached to tooth enamel 110. Intermolecular Van der Waal's forces stem from the large contact areas between a carbon-nanotube 302 and the tooth enamel 110. Some carbon-nanotubes 302 adhere to other carbon-nanotubes 302 forming bundles 304 of hundreds and even thousands of carbon-nanotubes 302 which further increase contact area. The physical properties of the carbon-nanotubes, such as the arrangement of carbon atoms, allow the carbon-nanotubes 302 to bend but maintain strength and structure which allows carbon-nanotubes 302 to maintain contact on an uneven tooth enamel 110 surface. Uneven surfaces typically prevent Van der Waal's forces from forming.

Figure 4:
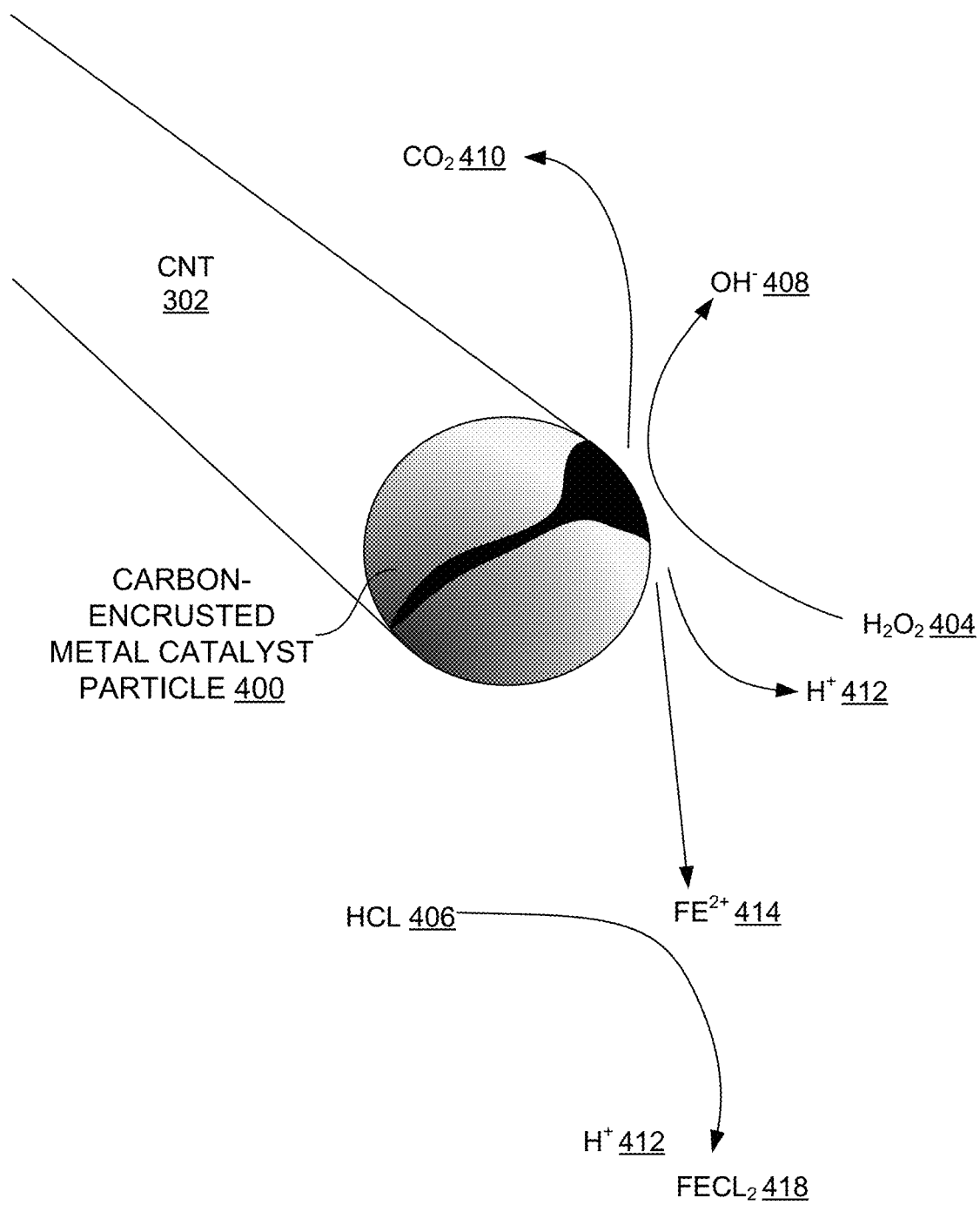
FIG. 4 is a block diagram of a carbon-encrusted metal catalyst particle.

FIG. 4 is a block diagram of a carbon-encrusted metal catalyst particle 400. After the growing of the carbon-nanotube 302 deactivates, a carbon-encrusted metal catalyst particle 400 particle is left on the carbon-nanotube 302. The carbon-encrusted metal catalyst particle 400 can affect the properties of the carbon-nanotube 302 and could potentially reduce adhesion of the carbon-nanotube 302 onto other surfaces. The carbon-nanotube 302 is treated with mixture of Hydrogen Peroxide 404 and Hydrochloric Acid 406 in order to remove the impurities such as the carbon-encrusted metal catalyst particle 400. The hydrogen peroxide 404 reacts with and dissolves the carbon on the surface of the carbon-encrusted catalyst particle 400, producing hydroxide 408, carbon dioxide 410, and hydrogen gas 412. The exposed metal of the carbon-encrusted catalyst produces metal ions, if iron was used as the metal catalyst particle, ferrous ions 414 would be released. The hydrochloric acid 406 then reacts with those ferrous ions 414 and dissolves them producing hydrogen gas 412 and iron chloride 418.

Figure 5:
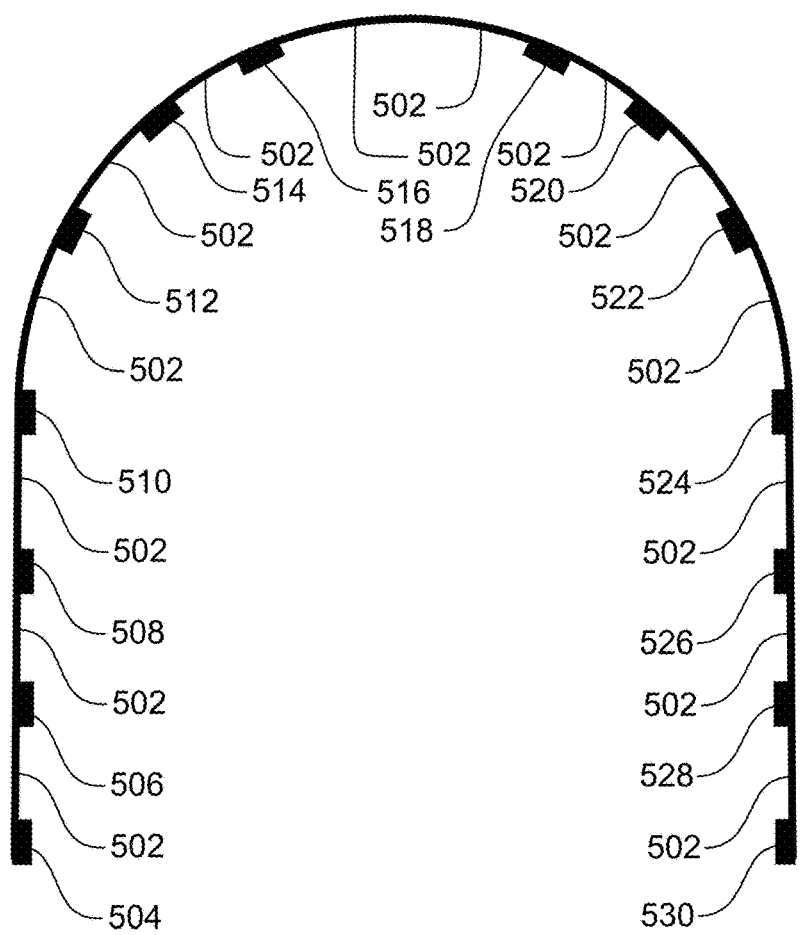
FIG. 5 is a block diagram of an overview of a carbon-nanotube tooth-bonding apparatus, according to an implementation.

FIG. 5 is a block diagram of an overview of a carbon-nanotube tooth-bonding apparatus 500, according to an implementation. Apparatus 500 can be described as a single-bonded archwire.

Apparatus 500 includes an archwire 502 and a plurality of carbon-nanotube bonding substrates 504, 506, 508, 510, 512, 514, 516, 518, 520, 522, 524, 526, 528 and 530. Each of the plurality of carbon-nanotube bonding substrates 504-530 are permanently fabricated to the archwire 502 at fixed positions of the archwire 502.

Figure 8:
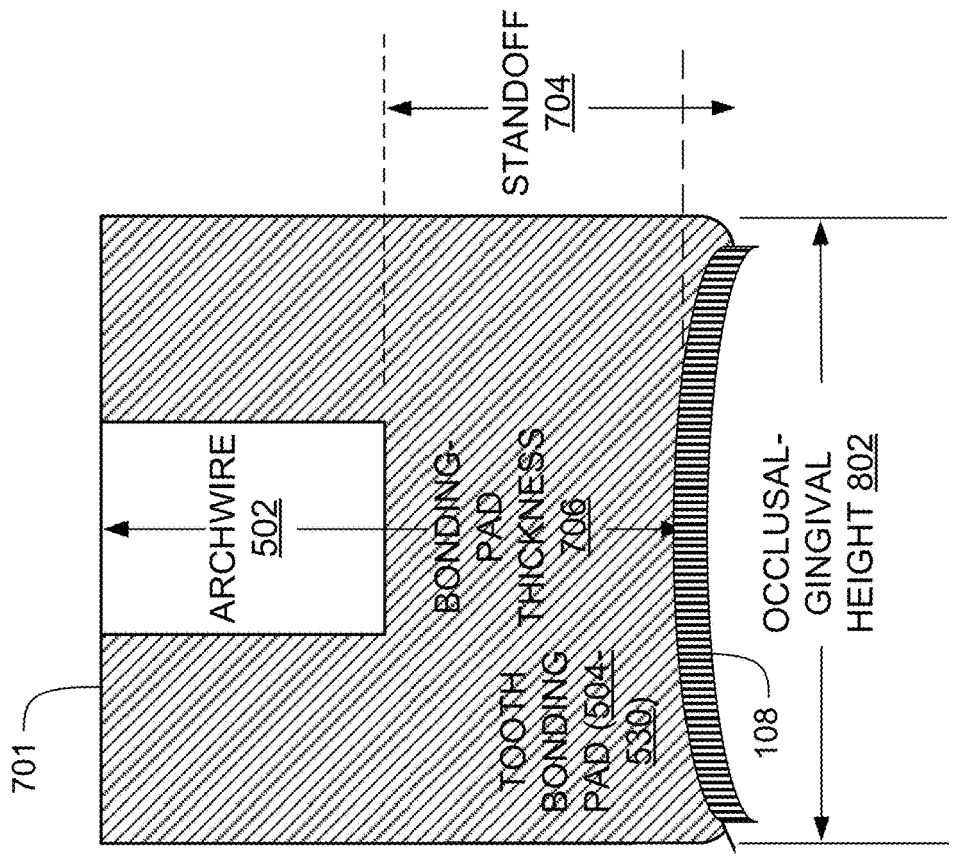
FIG. 8 is a distal or mesial view of a cross section block diagram of an apparatus according to an implementation illustrating an archwire exiting or protruding from a side of a carbon-nanotube bonding substrate.

An important feature in some implementations of apparatus 500 is that the apparatus 500 does not have or include an orthodontic bracket. The lack of an orthodontic bracket simplifies the fabrication of the apparatus 500. The lack of an orthodontic bracket also improves the comfort of a patient to which the apparatus 500 is applied. The absence of an orthodontic bracket provides a lower physical profile and a smaller height dimension, as shown in FIG. 8. The lower physical profile of apparatus 500 positions the archwire 502 further away from the inside of the cheek of the patient to which the apparatus 500 is applied, thus reducing friction of the inside of the cheek on the archwire 502, and thus improving comfort of the patient to which the apparatus 500 is applied.

Apparatus 500 can be implemented as an enabling appliance for orthodontic patients who, without prior treatment using apparatus 500, would not be practical candidates for complete and finishing orthodontic treatment with other removable orthodontic appliance systems, as described in greater detail in FIG. 25 below.

Figure 26:
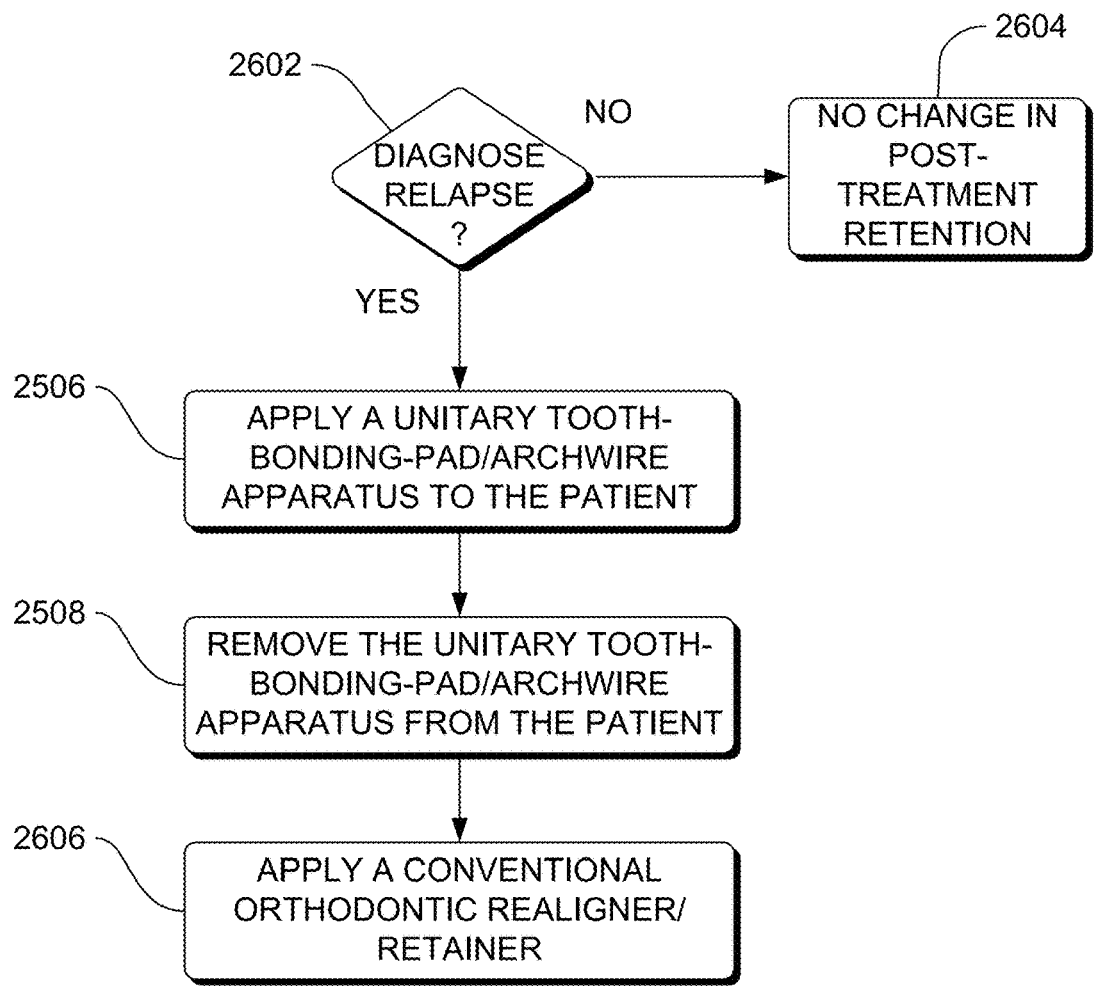
FIG. 26 is a flowchart of a method to implement a carbon-nanotube tooth-bonding apparatus, to correct orthodontic relapse.

For correction of orthodontic relapse, where the degree of relapse is outside the range of treatment of a conventional realigner-retainer appliance, apparatus 500 is implemented to bring the degree of correction needed back within range of a realigner or a retainer, as described in greater detail in FIG. 26.

Apparatus 500 can be implemented in order to facilitate the implementation of interceptive removable orthodontic devices for patients in a mixed dentition age range. For patients who have one or more teeth positioned such that the implementation of interceptive devices would be contraindicated, these problematically positioned teeth can be moved into positions by apparatus 500 in which the positions permit the implementation of these interceptive appliances. Interceptive orthodontic appliances include Frankel orthodontic appliances, Schwarz orthodontic appliances and Bionator orthodontic appliances, as described in greater detail in FIG. 27.

In addition apparatus 500 can be implemented as a single appliance treatment for complete orthodontic treatment in cases of minor orthodontic malocclusions. For example, in cases where a dental malocclusion consists of only minor tooth displacements, such as buccal-lingual displacements, rotations, tipping, and vertical height discrepancies, complete orthodontic treatment can be obtained with the application of apparatus 500. Following completion of orthodontic treatment using apparatus 500, any conventional retainer, such as a Hawley orthodontic appliance can be implemented to retain the orthodontic result, as described in greater detail in FIG. 28.

Apparatus 500 can be implemented prior to crown and bridge work in dentistry. When one or more of teeth that are to be prepared for crowns or as abutments for bridgework are in less than ideal positions, apparatus 500 can be implemented to better position these teeth for stress bearing associated with chewing forces, and also to allow for a more aesthetically appearing cosmetic result. Short term correction involving apparatus 500 aligns the anterior teeth so that conservative crown preparation will allow for a cosmetically ideal result, as described in greater detail in FIG. 29.

In some implementations of apparatus 500, the materials of the archwire 502 and/or the carbon-nanotube bonding substrates 504-530 include 0.0-5.5% iron, 7.0 to 9.0% aluminum, 3.0-5.5% nickel, 1.0-8.0% zinc, 0-2.5% manganese and the remainder being copper, or any other material that will work with conventional approved orthodontic bonding systems implemented for orthodontic bracket placement. The geometry of the carbon-nanotube bonding substrates 504-530 are of standardized bracket base form, derived from statistical tooth geometry data for labial and buccal tooth surfaces.

In the implementation shown in FIG. 5, the apparatus 500 includes 14 carbon-nanotube bonding substrates 504-530. However, other implementations can be fabricated, with any number of carbon-nanotube bonding substrates, such as 10 carbon-nanotube bonding substrates, 11 carbon-nanotube bonding substrates, 12 carbon-nanotube bonding substrates, 13 carbon-nanotube bonding substrates, 15 carbon-nanotube bonding substrates or 16 carbon-nanotube bonding substrates. The disclosure herein is not limited by the number of carbon-nanotube bonding substrates.

The locations for the carbon-nanotube bonding substrates 504-530 on the archwire 502 in FIG. 5 is one implementation. Variation among population bases and future applications associated with evolving treatment modalities alter the exact location of these carbon-nanotube bonding substrates 504-530 on the archwire 502. Additionally, the archwire 502 and carbon-nanotube bonding substrates 504-530 can be custom fabricated for a selected patient based on full arch impressions, optical or infrared scans, or calibrated photography, thus many variations in the locations for the carbon-nanotube bonding substrates 504-530 on the archwire 502 are contemplated.

In some implementations, the contours of the carbon-nanotube bonding substrates 504-530 are in accordance with existing statistical norms of the labial and buccal surfaces of the teeth. The size of the carbon-nanotube bonding substrates 504-530 are varied slightly to allow for the different force per unit deflection of the different diameter archwires.

In some implementations of apparatus 500, each of the carbon-nanotube bonding substrates have an orientation to the archwire 502 such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In further implementations, the carbon-nanotube bonding substrates are accurately appositioned with labial and buccal aspects at occlusal-gingival center and mesial-distal center to the extent that the human teeth that are not in orthodontically correct positions will experience corrective orthodontic forces moving the human teeth toward orthodontically correct positions.

In some implementations of apparatus 500, each of the carbon-nanotube bonding substrates includes at least one contour of each of the carbon-nanotube bonding substrates being produced from existing statistical norms of the labial and buccal surfaces of the teeth.

In some implementations of apparatus 500, the archwire 502 includes a nickel-titanium (NiTi) alloy metal. In some implementations of apparatus 500, the archwire 502 includes a thermally activated nickel-titanium (NiTi) alloy metal. In some implementations of the thermally activated NiTi alloy, force activation occurs at approximately 27 degrees Celsius and approximately 81 degrees Fahrenheit. Other metals that the archwire 502 can be made of include beta-Titanium, beta-Titanium-nickel, Titanium-carbide, Titanium Molybdenum alloys, stainless steel and/or nickel-cobalt alloys. In some implementations of apparatus 500, the archwire 502 includes stainless steel. In some implementations of apparatus 500, the archwire 502 includes gold. In some implementations of apparatus 500, the archwire 502 includes ceramic coated nickel titanium and stainless steel.

In some implementations of apparatus 500, the archwire 502 includes a diameter selected from the group of diameters consisting of 0.12 inches round, 0.14 inches round, 0.16 inches round, and 0.16×0.16 inches rectangular cross section.

In some implementations of apparatus 500, the archwire 502 includes a tooth-color as a result of manufacturing with epoxy coatings or other tooth-colored surfaces. Carbon-nanotube bonding substrates 504, 506, 508, 510, 512, 514, 516, 518, 520, 522, 524, 526, 528 and 530 can be removeably attached to any surface of a tooth.

While the apparatus 500 is not limited to any particular archwire 502 and carbon-nanotube bonding substrates 504-530, for sake of clarity a simplified archwire 502 and carbon-nanotube bonding substrates 504-530 are described.

Apparatus Implementations

In the previous section, a system level overview of the operation of an implementation was described. In this section, the particular apparatus of such an implementation are described by reference to a series of diagrams.

Figure 6:
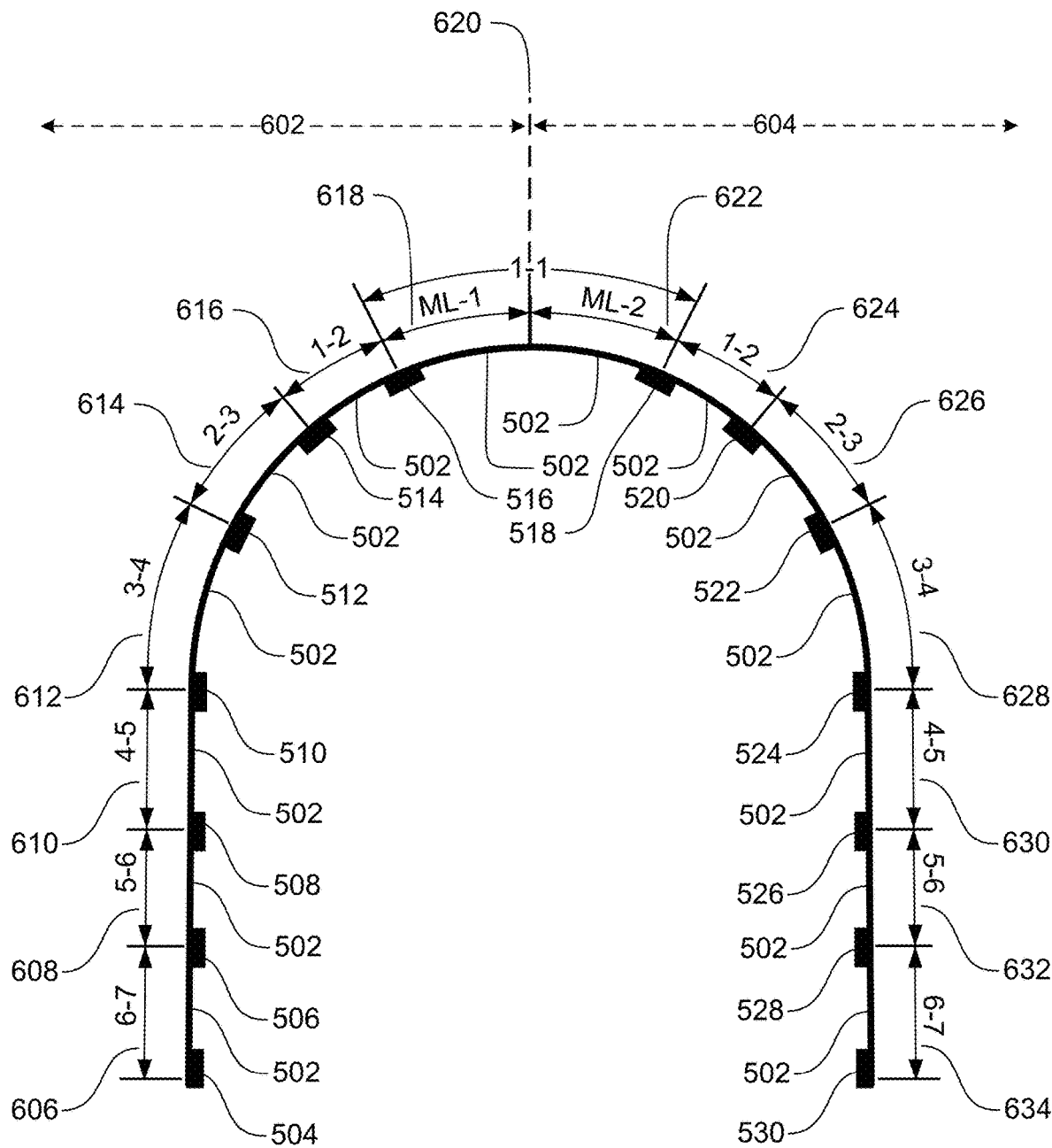
FIG. 6 is a block diagram of an overview of a carbon-nanotube tooth-bonding apparatus, according to an implementation and illustrating dimensions between carbon-nanotube bonding substrates.

FIG. 6 is a block diagram of an overview of a carbon-nanotube tooth-bonding apparatus 600, according to an implementation and illustrating dimensions between carbon-nanotube bonding substrates. Apparatus 600 is a carbon-nanotube tooth-bonding apparatus that does not have or include an orthodontic bracket, which as a result of the absent orthodontic bracket can be fabricated easily, simply and inexpensively, and that has a low physical profile and a smaller height dimension that positions the archwire 502 further away from the inside of the cheek of a patient to which the apparatus 600 is applied, thus reducing friction of the inside of the cheek on the archwire, and thus improving comfort of the patient to which the apparatus 600 is applied.

Each archwire includes two sides 602 and 604.

In side 602, the fixed dimensions between the centers of carbon-nanotube bonding substrates 504 and 506 is "space 6-7" 606, the fixed dimensions between the centers of carbon-nanotube bonding substrates 506 and 508 is "space 5-6" 608, the fixed dimensions between the centers of carbon-nanotube bonding substrates 508 and 510 is "space 4-5" 610, the fixed dimensions between the centers of carbon-nanotube bonding substrates 510 and 512 is "space 3-4" 612, the fixed dimensions between the centers of carbon-nanotube bonding substrates 512 and 514 is "space 2-3" 614, the fixed dimensions between the centers of carbon-nanotube bonding substrates 514 and 516 is "space 1-2" 616, the fixed dimensions between the centers of carbon-nanotube bonding substrate 516 and the midline 620 of the apparatus 600 is "ML-1" 618.

In side 604, the fixed dimensions between the midline 620 and the center of carbon-nanotube bonding substrate 518 is "ML-2" 622, the fixed dimensions between the centers of carbon-nanotube bonding substrates 518 and 520 is "space 1-2" 624, the fixed dimensions between the centers of carbon-nanotube bonding substrates 520 and 522 is "space 2-3" 626, the fixed dimensions between the centers of carbon-nanotube bonding substrates 522 and 524 is "space 3-4" 628, the fixed dimensions between the centers of carbon-nanotube bonding substrates 524 and 526 is "space 4-5" 630, the fixed dimensions between the centers of carbon-nanotube bonding substrates 526 and 528 is "space 5-6" 632, the fixed dimensions between the centers of carbon-nanotube bonding substrates 528 and 530 is "Space 6-7" 634.

In the implementation illustrated in FIG. 6, each side 602 and 604, is symmetrical. The geometry and the dimensions of the archwire 502 and the carbon-nanotube bonding substrates 504-530 are symmetrical between the two sides 602 and 604, and also the positions of the carbon-nanotube bonding substrates 504-530 on the archwire 502 are symmetrical between the two sides 602 and 604. Because of the symmetry of sides 602 and 604, "Space 6-7" 606 has the same dimensions as "Space 6-7" 634, "Space 5-6" 608 has the same dimensions as "Space 5-6" 632, "Space 4-5" 610 has the same dimensions as "Space 4-5 630, "Space 6-4" 612 has the same dimensions as "Space 3-4" 628, "Space 2-3" 614 has the same dimensions as "Space 2-3" 626, "Space 1-2" 616 has the same dimensions as "Space 1-2" 624 and "ML-1" 618 has the same dimensions as "ML-2" 1.

Other implementations of apparatus 600 that are not illustrated are asymmetrical in one or more aspects.

In some implementations, carbon-nanotube bonding substrates 506 and 528 for the first permanent molars have a thinner thickness than the thickness for the carbon-nanotube bonding substrates in the close vicinity, such as carbon-nanotube bonding substrates 504 and 508, and 530 and 526 because in some patients, the first buccal surfaces of the first permanent molars is more pronounced or protruding than the first buccal (outside) surfaces of the adjacent teeth. In some implementations carbon-nanotube bonding substrates 512 and 522 for the canine teeth have a thinner thickness than the thickness for the carbon-nanotube bonding substrates in the close vicinity, such as carbon-nanotube bonding substrates 510 and 514, and 524 and 520 because in some patients, the first buccal surfaces of the canine teeth is more pronounced or more protruding than the first buccal surfaces of the adjacent teeth.

Figure 7:
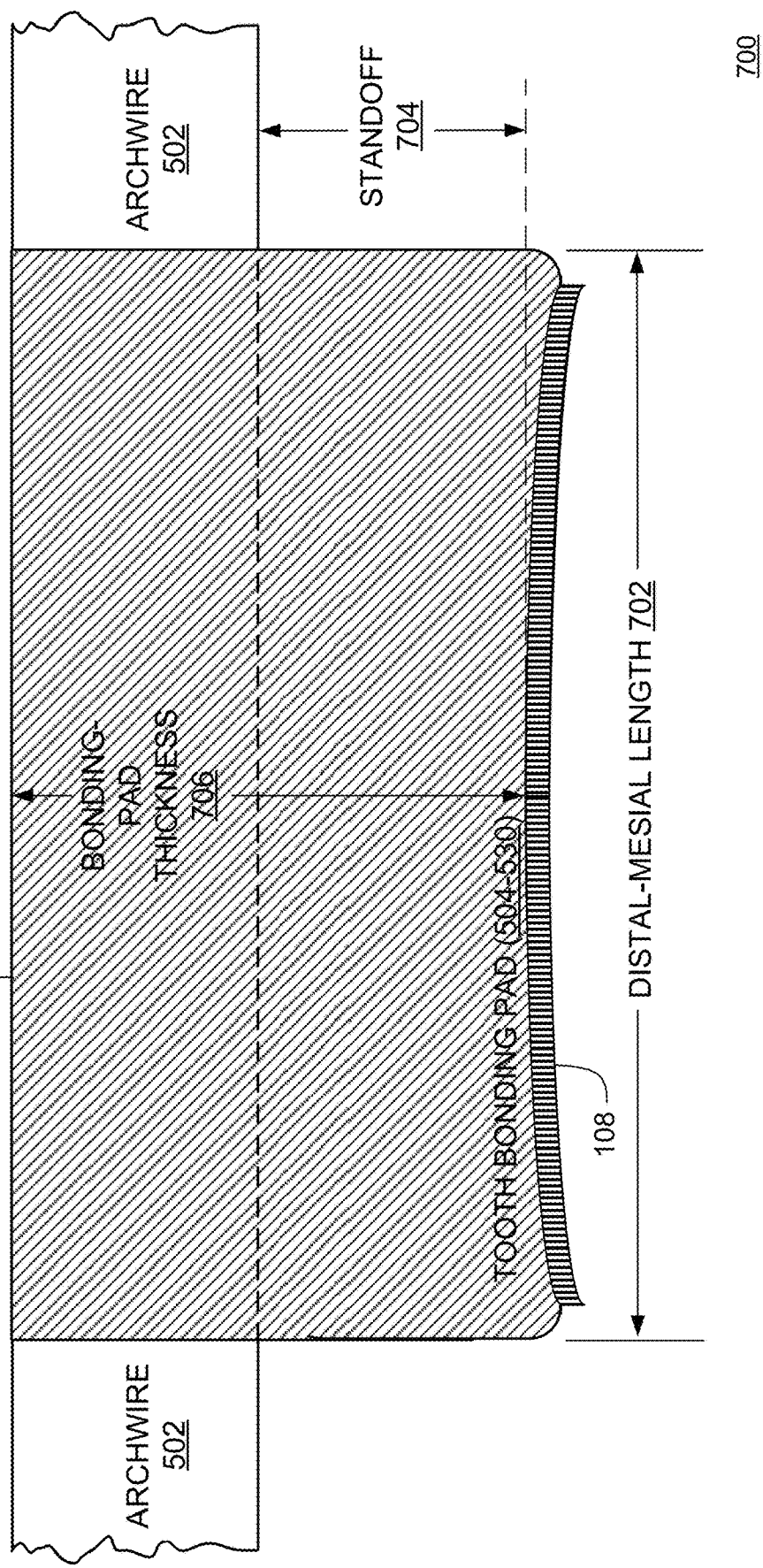
FIG. 7 is an occlusal view of a cross section block diagram of an apparatus according to an implementation illustrating an archwire exiting or protruding from a side of a carbon-nanotube bonding substrate.

FIG. 7 is an occlusal view of a cross section block diagram of apparatus 700 according to an implementation illustrating an archwire exiting or protruding from a side of a carbon-nanotube bonding substrate. Apparatus 700 is a carbon-nanotube tooth-bonding apparatus that does not have or include an orthodontic bracket, which as a result of the absent orthodontic bracket, can be fabricated easily, simply and inexpensively, and that has a low physical profile and a smaller height dimension that positions the archwire 502 further away from the inside of the cheek of a patient to which the apparatus 700 is applied, thus reducing friction of the inside of the cheek on the archwire 502, and thus improving comfort of the patient to which the apparatus 700 is applied.

In apparatus 700, the archwire 502 is permanently fabricated into the side 701 of the matter of the carbon-nanotube bonding substrate. The carbon-nanotube bonding substrate in apparatus 700 is any one of the carbon-nanotube bonding substrates 504-530 shown in FIG. 5 and FIG. 6. In apparatus 700, most of the outside surface of the archwire 502 that is in close proximity to the carbon-nanotube bonding substrates 504-530 is fabricated into the carbon-nanotube bonding substrates 504-530. In the implementation shown in FIG. 7, the carbon-nanotube bonding substrate includes a mesial-distal length 702 in a range of 1.5 millimeters (mm) to 3.0 mm, a standoff 704 in the range of 0.1 mm and 2.0 mm and a bonding-pad thickness 706 in a range of 0.10 mm to 2.0 mm. In no case is the bonding-pad thickness 706 greater than the standoff 704 plus the diameter of the archwire 502. However, the disclosure herein is not limited to any particular dimensions of the mesial-distal length 702, standoff 704, bonding-pad thickness 706, carbon-nanotube bonding substrates 504-530 or the archwire 502.

In apparatus 700, most of the outside surface of the archwire 502 is fabricated into the carbon-nanotube bonding substrates 504-530, as described in greater detail in FIG. 8.

The absence of an orthodontic bracket in apparatus 700 provides a lower profile and a smaller bonding-pad thickness 706. The smaller bonding-pad thickness 706 of apparatus 700 positions the archwire 502 closer to the gingival and thus further away from the inside of the cheek of the patient, thus reducing friction between the inside of the cheek and the archwire 502, and therefore improving comfort of the patient.

FIG. 8 is a distal or mesial view of a cross section block diagram of apparatus 700 according to an implementation illustrating an archwire exiting or protruding from a side of a carbon-nanotube bonding substrate.

In apparatus 700, the archwire 502 is permanently fabricated into the matter of a carbon-nanotube bonding substrate. The carbon-nanotube bonding substrate in apparatus 700 is any one of the carbon-nanotube bonding substrates 504-530 shown in FIG. 5 and FIG. 6. In the implementation shown in FIG. 8, the carbon-nanotube bonding substrate includes a bonding-pad thickness 706 in a range of 1.5 mm to 4 mm and a bonding-pad thickness 706 in a range of 0.10 mm to 2.0 mm. However, the disclosure herein is not limited to any particular dimensions of the carbon-nanotube bonding substrates or the archwire 502.

As shown in FIG. 8, most of the outside surface of the archwire 502 of apparatus 700 is fabricated into the carbon-nanotube bonding substrates 504-530. In the implementation shown in FIG. 8, about 75% (3 of 4 surfaces) of the outside surface of the archwire 502 of apparatus 700 is fabricated into the carbon-nanotube bonding substrates 504-530. The archwire 502 of apparatus 700 is fabricated into the side 701 of the carbon-nanotube bonding substrates 504-530.

Figure 9:
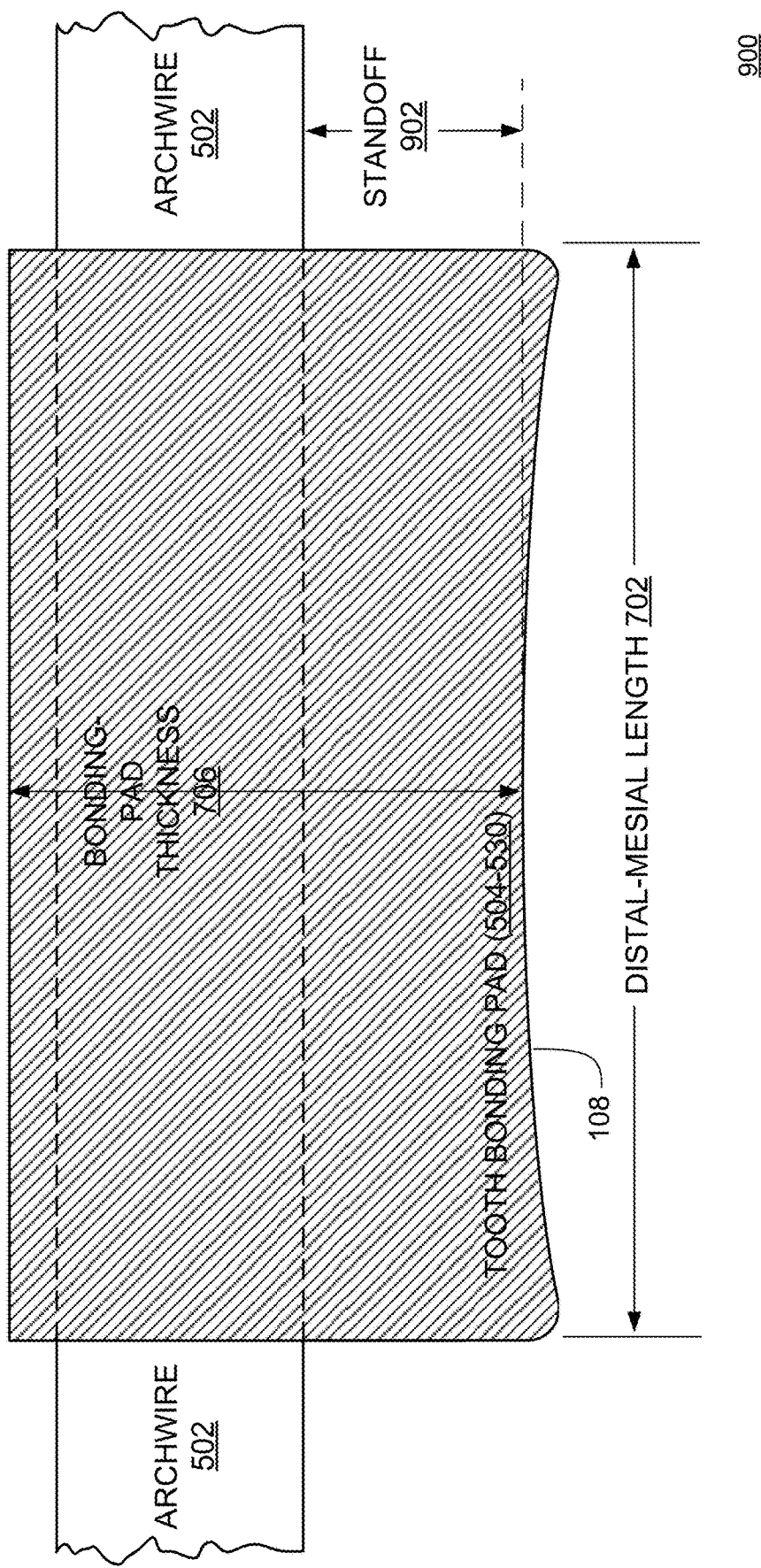
FIG. 9 is an occlusal view of a cross section block diagram of an apparatus according to an implementation illustrating an archwire exiting or protruding from an interior of a carbon-nanotube bonding substrate.

FIG. 9 is an occlusal view of a cross section block diagram of apparatus 900 according to an implementation illustrating an archwire exiting or protruding from an interior of a carbon-nanotube bonding substrate. Apparatus 900 is a carbon-nanotube tooth-bonding apparatus that does not have or include an orthodontic bracket, which as a result of the absent orthodontic bracket, can be fabricated easily, simply and inexpensively, and that has a low physical profile and a smaller height dimension that positions the archwire 502 further away from the inside of the cheek of a patient to which the apparatus 900 is applied, thus reducing friction of the inside of the cheek on the archwire 502, and thus improving comfort of the patient to which the apparatus 900 is applied.

In apparatus 900, the archwire 502 extends through the interior of the matter of the carbon-nanotube bonding substrate in FIG. 9. The carbon-nanotube bonding substrate in apparatus 900 in FIG. 9 is any one of the carbon-nanotube bonding substrates 504-530 shown in FIG. 5 and FIG. 6. In apparatus 900, the archwire 502 passes through the carbon-nanotube bonding substrate in FIG. 9. In the implementation shown in FIG. 9, the carbon-nanotube bonding substrate includes a mesial-distal length 702 in a range of 1.5 mm to 3.0 mm, a standoff 902 in the range of 0.125 mm to 0.140 mm and a carbon-nanotube bonding substrate thickness 706 in a range of 0.125 mm to 1.5 mm. In no case is the bonding-pad thickness 706 greater than the standoff 902 plus the diameter of the archwire 502. However, the disclosure herein is not limited to any particular dimensions of the mesial-distal length 702, standoff 902, carbon-nanotube bonding substrate thickness 706, carbon-nanotube bonding substrates 504-530 or the archwire 502. The standoff 902 shown in FIG. 9 is a medium dimension of the standoff 902. In some cases in which the dimension of standoff 902 is de minimus, the standoff 902 is approx 0.125 mm.

Figure 10:
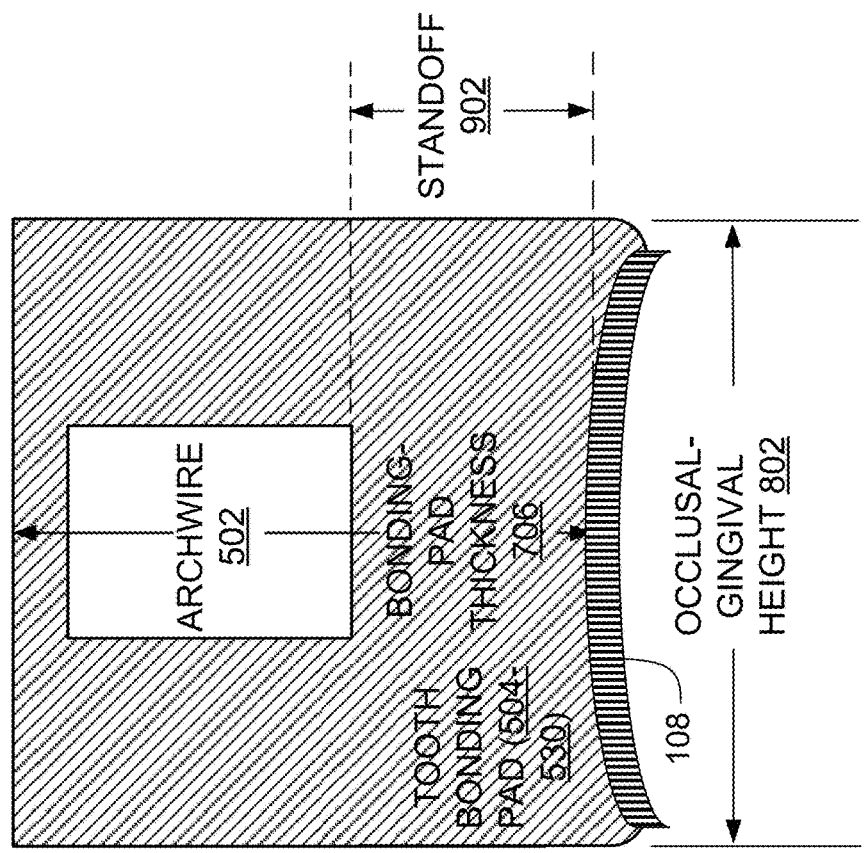
FIG. 10 is a distal or mesial view of a cross section block diagram of an apparatus according to an implementation illustrating an archwire exiting or protruding from an interior of a carbon-nanotube bonding substrate.

In some implementations of apparatus 900, most of the outside surface of the archwire 502 is fabricated into the carbon-nanotube bonding substrates 504-530, as described in greater detail in FIG. 10. In some implementations of apparatus 900, the archwire 502 is permanently fabricated into the interior of the matter of the carbon-nanotube bonding substrate.

The absence of an orthodontic bracket in apparatus 900 provides a lower profile and a smaller standoff 902. The smaller standoff 902 of apparatus 900 positions the archwire 502 closer to the gingival and thus further away from the inside of the cheek of the patient, thus reducing friction between the inside of the cheek and the archwire 502, and therefore improving comfort of the patient.

FIG. 10 is a distal or mesial view of a cross section block diagram of apparatus 900 according to an implementation illustrating an archwire exiting or protruding from an interior of a carbon-nanotube bonding substrate.

In apparatus 900, the archwire 502 is permanently fabricated into the matter of a carbon-nanotube bonding substrate. The carbon-nanotube bonding substrate in apparatus 900 is any one of the carbon-nanotube bonding substrates 504-530 shown in FIG. 5 and FIG. 6. In the implementation shown in FIG. 10, the carbon-nanotube bonding substrate includes a mesial-distal length 702 in a range of 1.5 mm to 3.0 mm and a tooth-bonding thickness 706 in a range of 0.10 mm to 2.0 mm. However, the disclosure herein is not limited to any particular dimensions of the carbon-nanotube bonding substrates or the archwire 502.

As shown in FIG. 10, most of the outside surface of the archwire 502 of apparatus 900 is fabricated into the carbon-nanotube bonding substrates 504-530. In the implementation shown in FIG. 10, about 100% (4 of 4 surfaces) of the outside surface in close proximity to the archwire 502 of apparatus 900 is fabricated into the carbon-nanotube bonding substrates 504-530. The archwire 502 of apparatus 900 is fabricated into the interior of the carbon-nanotube bonding substrates 504-530.

In apparatus 900, most of the outside surface of the archwire 502 is fabricated into the interior of the carbon-nanotube bonding substrates 504-530. In the implementation shown in FIG. 9, the carbon-nanotube bonding substrate 504-530 includes a mesial-distal length 702 in a range of 1.5 mm to 3.0 mm and a bonding-pad thickness 706 in a range of 0.10 mm to 2.0 mm.

Figure 11:
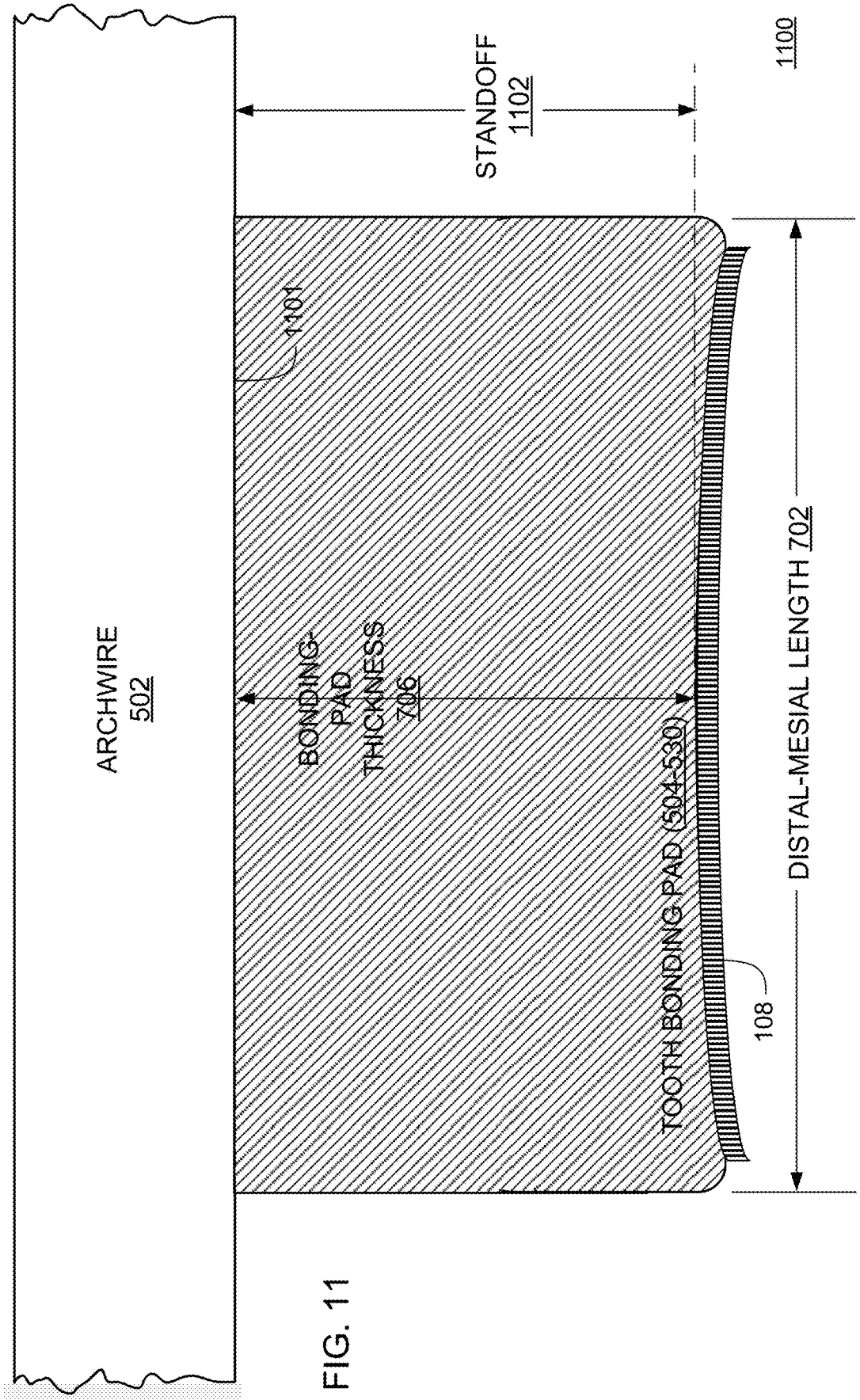
FIG. 11 is an occlusal view of a cross section block diagram of an apparatus according to an implementation illustrating an archwire removeably attached to a side of a carbon-nanotube bonding substrate.

FIG. 11 is an occlusal view of a cross section block diagram of apparatus 1100 according to an implementation illustrating an archwire removeably attached to a side of a carbon-nanotube bonding substrate. Apparatus 1100 is a carbon-nanotube tooth-bonding apparatus that does not have or include an orthodontic bracket, which as a result of the absent orthodontic bracket, can be fabricated easily, simply and inexpensively, and that has a low physical profile and a smaller height dimension that positions the archwire 502 further away from the inside of the cheek of a patient to which the apparatus 1100 is applied, thus reducing friction of the inside of the cheek on the archwire 502, and thus improving comfort of the patient to which the apparatus 1100 is applied.

In apparatus 1100, the archwire 502 is fabricated onto the side 1101 of the carbon-nanotube bonding substrate. The carbon-nanotube bonding substrate in apparatus 1100 is any one of the carbon-nanotube bonding substrates 504-530 shown in FIG. 5 and FIG. 6. In apparatus 1100, less than half of the outside surface of the archwire 502 that is in close proximity to the carbon-nanotube bonding substrates 504-530 is fabricated onto the carbon-nanotube bonding substrates 504-530. In the implementation shown in FIG. 11, the carbon-nanotube bonding substrate includes a mesial-distal length 702 in a range of 1.5 mm to 3.0 mm, a standoff 1102 in the range of 0.125 mm and 1.5 mm and a carbon-nanotube bonding substrate thickness 706 in a range of 0.1 mm to 2.0 mm. The bonding-pad thickness 706 is equal to the standoff 1102. However, the disclosure herein is not limited to any particular dimensions of the mesial-distal length 702, standoff 1102, carbon-nanotube bonding substrate thickness 706, carbon-nanotube bonding substrates 504-530 or the archwire 502.

Figure 12:
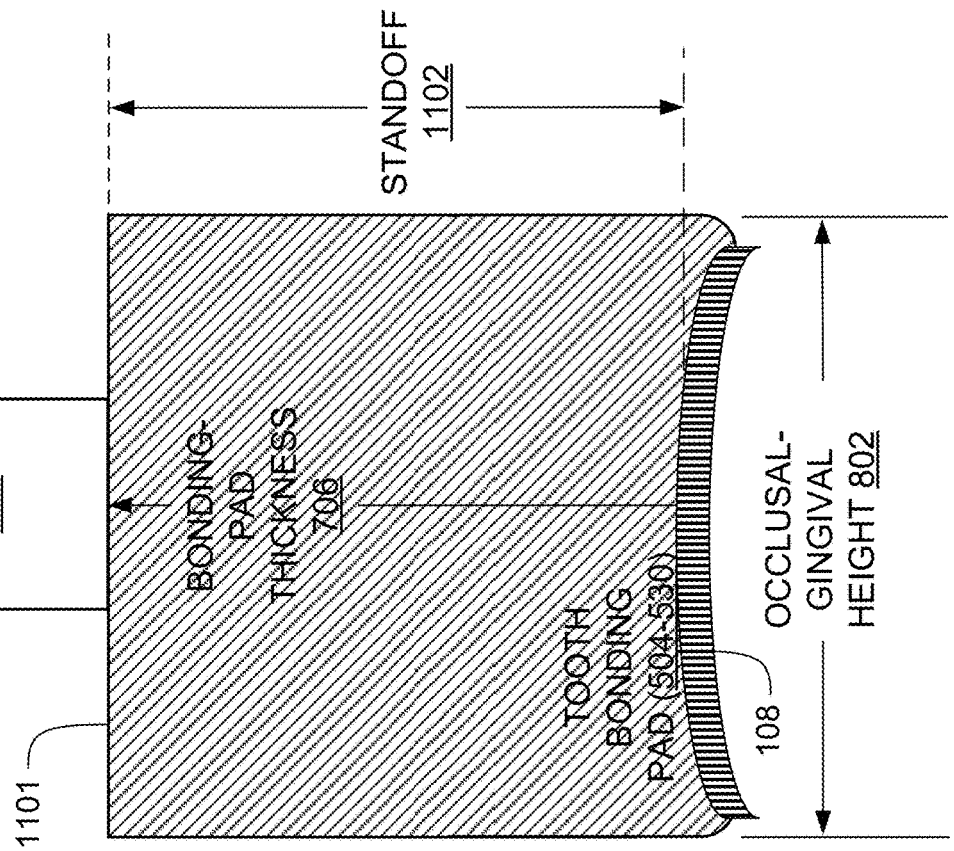
FIG. 12 is a distal or mesial view of a cross section block diagram of an apparatus according to an implementation illustrating an archwire removeably attached to a side of a carbon-nanotube bonding substrate.

In apparatus 1100, less than half of the outside surface of the archwire 502 is fabricated onto the carbon-nanotube bonding substrates 504-530, as described in greater detail in FIG. 12.

The absence of an orthodontic bracket in apparatus 1100 provides a lower profile and a smaller occlusal-gingival height 802. The smaller occlusal-gingival height 802 of apparatus 1100 positions the archwire 502 closer to the gingival and thus further away from the inside of the cheek of the patient, thus reducing friction between the inside of the cheek and the archwire 502, and therefore improving comfort of the patient.

FIG. 12 is a distal or mesial view of a cross section block diagram of apparatus 1100 according to an implementation illustrating an archwire removeably attached to a side of a carbon-nanotube bonding substrate.

In apparatus 1100, the archwire 502 is permanently fabricated onto the matter of a carbon-nanotube bonding substrate. The carbon-nanotube bonding substrate in apparatus 1100 is any one of the carbon-nanotube bonding substrates 504-530 shown in FIG. 5 and FIG. 6. In the implementation shown in FIG. 12, the carbon-nanotube bonding substrate includes a bonding-pad thickness 706 in a range of 0.10 mm to 2.0 mm and a mesial-distal length 702 in a range of 1.5 mm to 3.0 mm. However, the disclosure herein is not limited to any particular dimensions of the carbon-nanotube bonding substrates or the archwire 502.

As shown in FIG. 12, less than half of the outside surface of the archwire 502 of apparatus 1100 is fabricated onto the carbon-nanotube bonding substrates 504-530. In the implementation shown in FIG. 12, about 25% (1 of 4 surfaces) of the outside surface of the archwire 502 of apparatus 1100 is fabricated onto the carbon-nanotube bonding substrates 504-530. The archwire 502 of apparatus 1100 is fabricated onto the side 1101 of the carbon-nanotube bonding substrates 504-530.

In apparatus 1100, less than half of the outside surface of the archwire 502 is fabricated onto the side 1101 of the carbon-nanotube bonding substrates 504-530. In the implementation shown in FIGS. 11 and 13, the carbon-nanotube bonding substrate 504-530 includes a mesial-distal length 702 in a range of 1.5 mm to 3.0 mm and an occlusal-gingival height 802 in a range of 1.5 mm to 4 mm.

Figure 13:
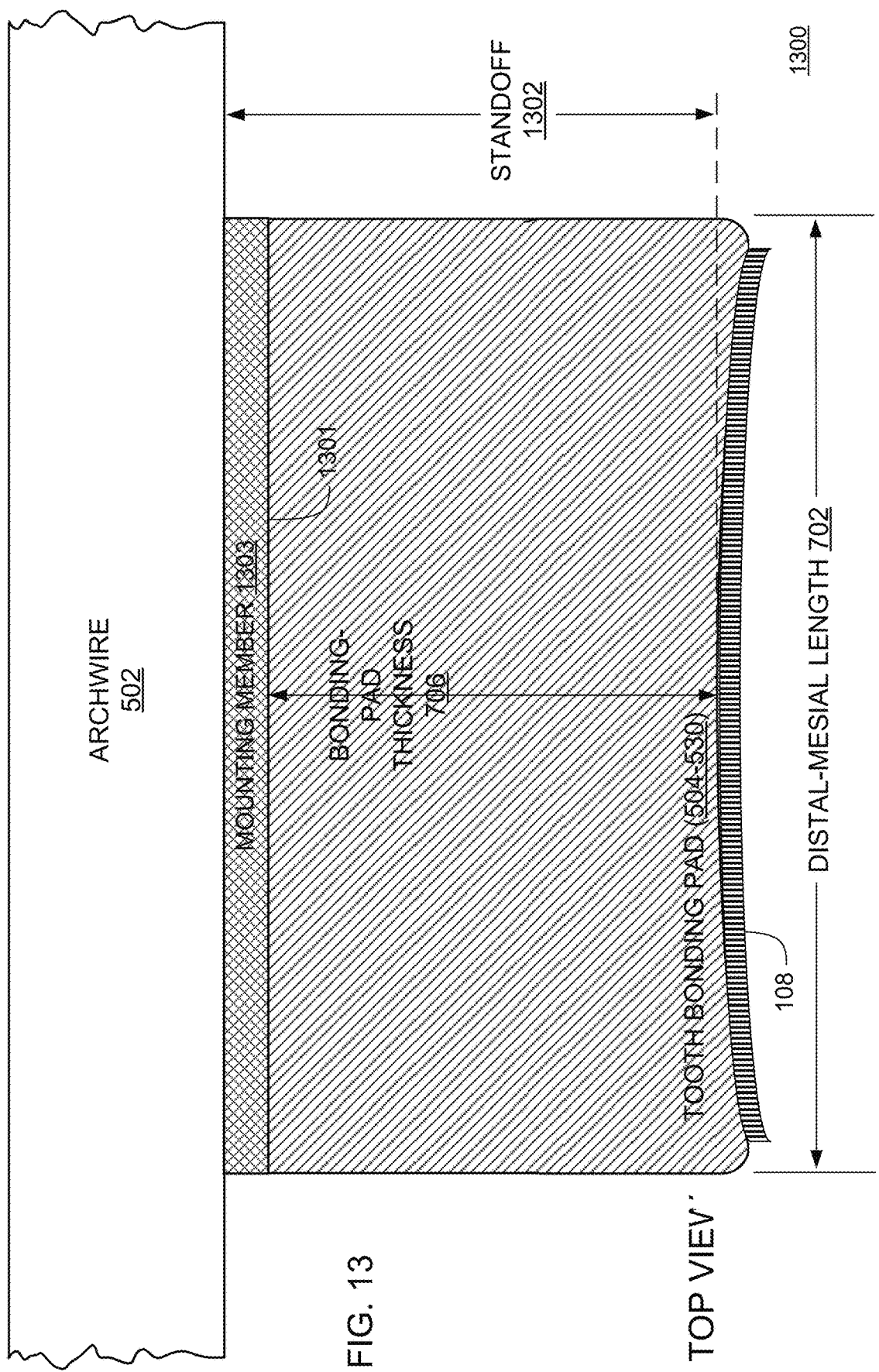
FIG. 13 is an occlusal view of a cross section block diagram of an apparatus according to an implementation illustrating an archwire indirectly attached to a side of a carbon-nanotube bonding substrate.

FIG. 13 is an occlusal view of a cross section block diagram of apparatus 1300 according to an implementation illustrating an archwire indirectly attached to a side of a carbon-nanotube bonding substrate. Apparatus 1300 is a carbon-nanotube tooth-bonding apparatus that does not have or include an orthodontic bracket, which as a result of the absent orthodontic bracket, can be attached easily, simply and inexpensively, and that has a low physical profile and a smaller height dimension that positions the archwire 502 further away from the inside of the cheek of a patient to which the apparatus 1300 is applied, thus reducing friction of the inside of the cheek on the archwire 502, and thus improving comfort of the patient to which the apparatus 1300 is applied.

In apparatus 1300, the archwire 502 is indirectly attached onto the side 1301 of the carbon-nanotube bonding substrate though a mounting member 1303. The carbon-nanotube bonding substrate in apparatus 1300 is any one of the carbon-nanotube bonding substrates 504-530 shown in FIG. 5 and FIG. 6. In apparatus 1300, none of the outside surface of the archwire 502 that is in close proximity to the carbon-nanotube bonding substrates 504-530 is directly attached to the carbon-nanotube bonding substrates 504-530 though the mounting member 1303. In the implementation shown in FIG. 13, the carbon-nanotube bonding substrate includes a mesial-distal length 702 in a range of 1.5 mm to 3.0 mm, a standoff 1302 in the range of 0.25 mm and 1.75 mm and an occlusal-gingival height 802 in a range of 1.5 mm to 4 mm. However, the disclosure herein is not limited to any particular dimensions of the mesial-distal length 702, standoff 1302, occlusal-gingival height 802, carbon-nanotube bonding substrates 504-530 or the archwire 502.

Figure 14:
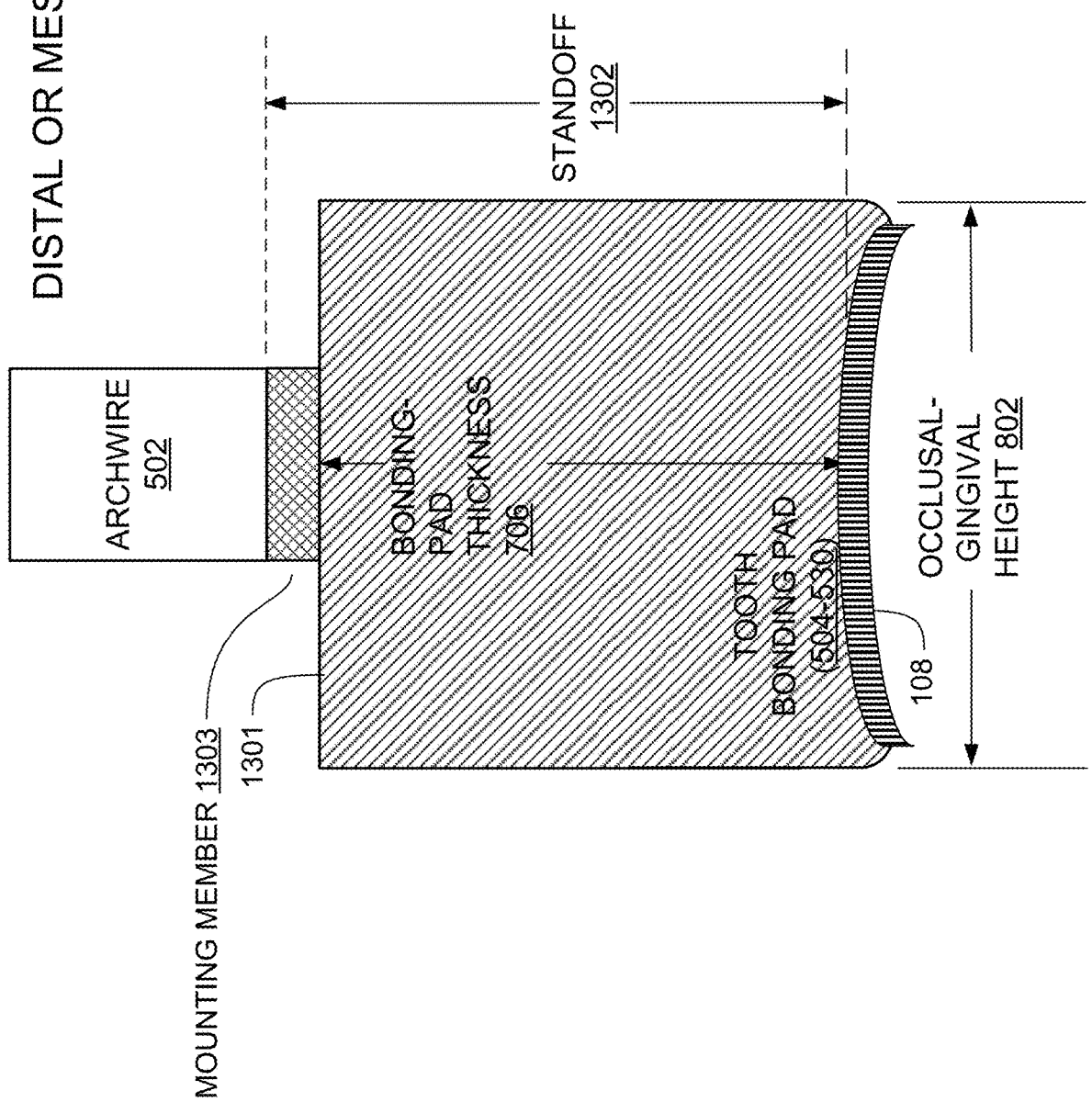
FIG. 14 is a distal or mesial view of a cross section block diagram of an apparatus according to an implementation illustrating an archwire removeably attached to a side of a carbon-nanotube bonding substrate.

In apparatus 1300, none of the outside surface of the archwire 502 is directly attached to the carbon-nanotube bonding substrates 504-530 though the mounting member 1303, as described in greater detail in FIG. 14.

The absence of an orthodontic bracket in apparatus 1300 provides a lower profile and a smaller occlusal-gingival height 802. The smaller occlusal-gingival height 802 of apparatus 1300 positions the archwire 502 closer to the gingival and thus further away from the inside of the cheek of the patient, thus reducing friction between the inside of the cheek and the archwire 502, and therefore improving comfort of the patient.

FIG. 14 is a distal or mesial view of a cross section block diagram of apparatus 1300 according to an implementation illustrating an archwire removeably attached to a side of a carbon-nanotube bonding substrate.

In apparatus 1300, the archwire 502 is permanently attached to the matter of a carbon-nanotube bonding substrate through a mounting member 1303. The carbon-nanotube bonding substrate in apparatus 1300 is any one of the carbon-nanotube bonding substrates 504-530 shown in FIG. 5 and FIG. 6. In the implementation shown in FIG. 14, the carbon-nanotube bonding substrate includes a bonding-pad thickness 706 in a range of 0.10 mm to 2.0 mm and a mesial-distal length 702 in a range of 1.5 mm to 3.0 mm. However, the disclosure herein is not limited to any particular dimensions of the carbon-nanotube bonding substrates or the archwire 502.

As shown in FIG. 14, none of the outside surface of the archwire 502 of apparatus 1300 is attached directly onto the carbon-nanotube bonding substrates 504-530. In the implementation shown in FIG. 14, 0% (0 of 4 surfaces) of the outside surface of the archwire 502 of apparatus 1300 is directly attached to the carbon-nanotube bonding substrates 504-530. Instead, the archwire 502 of apparatus 1300 is attached to the side 1301 of the carbon-nanotube bonding substrates 504-530 through the mounting member 1303.

FIGS. 7, 8, 9, 10, 11, 12, 13 and 14 show a curved surface onto which the carbon-nanotube bonding substrate adheres to the curved surface of the tooth. The geometry of the curved surface in FIGS. 7, 8, 9, 10, 11, 12, 13 and 14 is merely illustrative, and not necessarily exemplary and not limiting because curved surfaces of other geometries are within contemplation to accommodate tooth surface curvature geometries of a large variety.

In apparatus 1300, none of the outside surface of the archwire 502 is attached directly to the side 1301 of the carbon-nanotube bonding substrates 504-530. In the implementation shown in FIGS. 13 and 16, the carbon-nanotube bonding substrate 504-530 includes a mesial-distal length 702 in a range of 1.5 mm to 3.0 mm and a bonding-pad thickness 706 in a range of 1.5 mm to 4 mm.

The archwire 502 is depicted in FIGS. 8, 10, 12 and 14 as being rectangular in cross-section. However, the geometry of the archwire can be any variety of geometries in cross-section, such as round, oval, eliptical, square, pentagular, heptangular, octangular, decangular, or asymmetrical.

Figure 15:
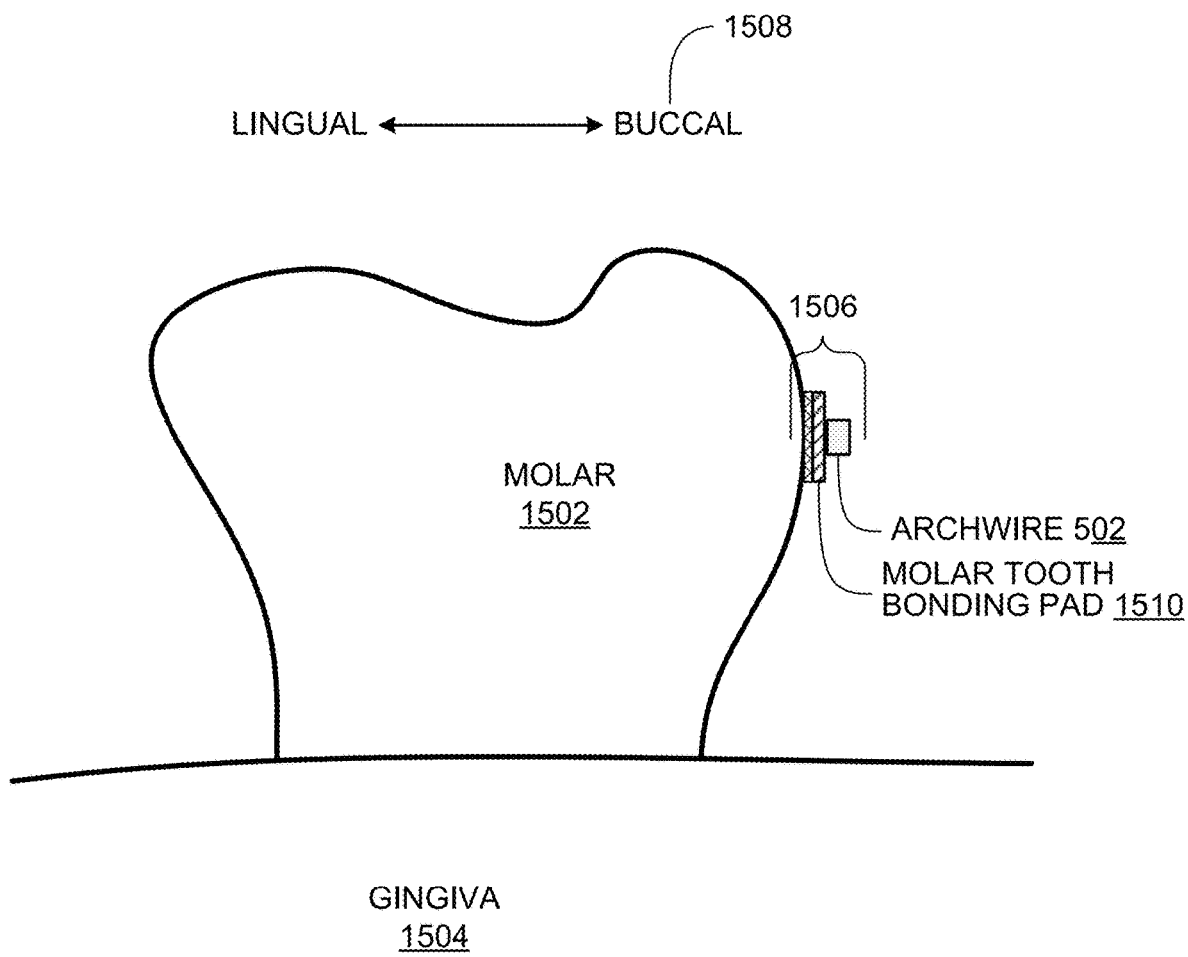
FIG. 15 is a block diagram of a molar carbon-nanotube tooth-bonding apparatus applied to a molar tooth, according to an implementation.

FIG. 15 is a block diagram 1500 of a molar carbon-nanotube tooth-bonding apparatus applied to a molar tooth, according to an implementation. FIG. 15 shows a molar tooth 1502 situated in gingival tissue 1504. A molar carbon-nanotube tooth-bonding apparatus 1506 that is applied to the buccal surface 1508 of the molar tooth 1502. The molar carbon-nanotube tooth-bonding apparatus 1506 includes a molar tooth bonding pad 1510 that is removeably attached to the buccal surface 1508 of the molar tooth 1502. An archwire 502 of the molar carbon-nanotube tooth-bonding apparatus 1506 is attached to the molar tooth bonding pad 1510.

Apparatus 500, apparatus 600, apparatus 700, apparatus 900, apparatus 1100 and apparatus 1300 are implementations of the molar carbon-nanotube tooth-bonding apparatus 1506. The molar carbon-nanotube tooth-bonding apparatus 1506 does not have or include an orthodontic bracket, which as a result of the absent orthodontic bracket, the molar carbon-nanotube tooth-bonding apparatus 1506 can be fabricated easily, simply and inexpensively, and the molar carbon-nanotube tooth-bonding apparatus 1506 has a low physical profile and a smaller height dimension that positions the archwire 502 further away from the inside of the cheek of the patient, thus reducing friction of the inside of the cheek on the archwire 502, and thus improving comfort of the patient.

Figure 16:
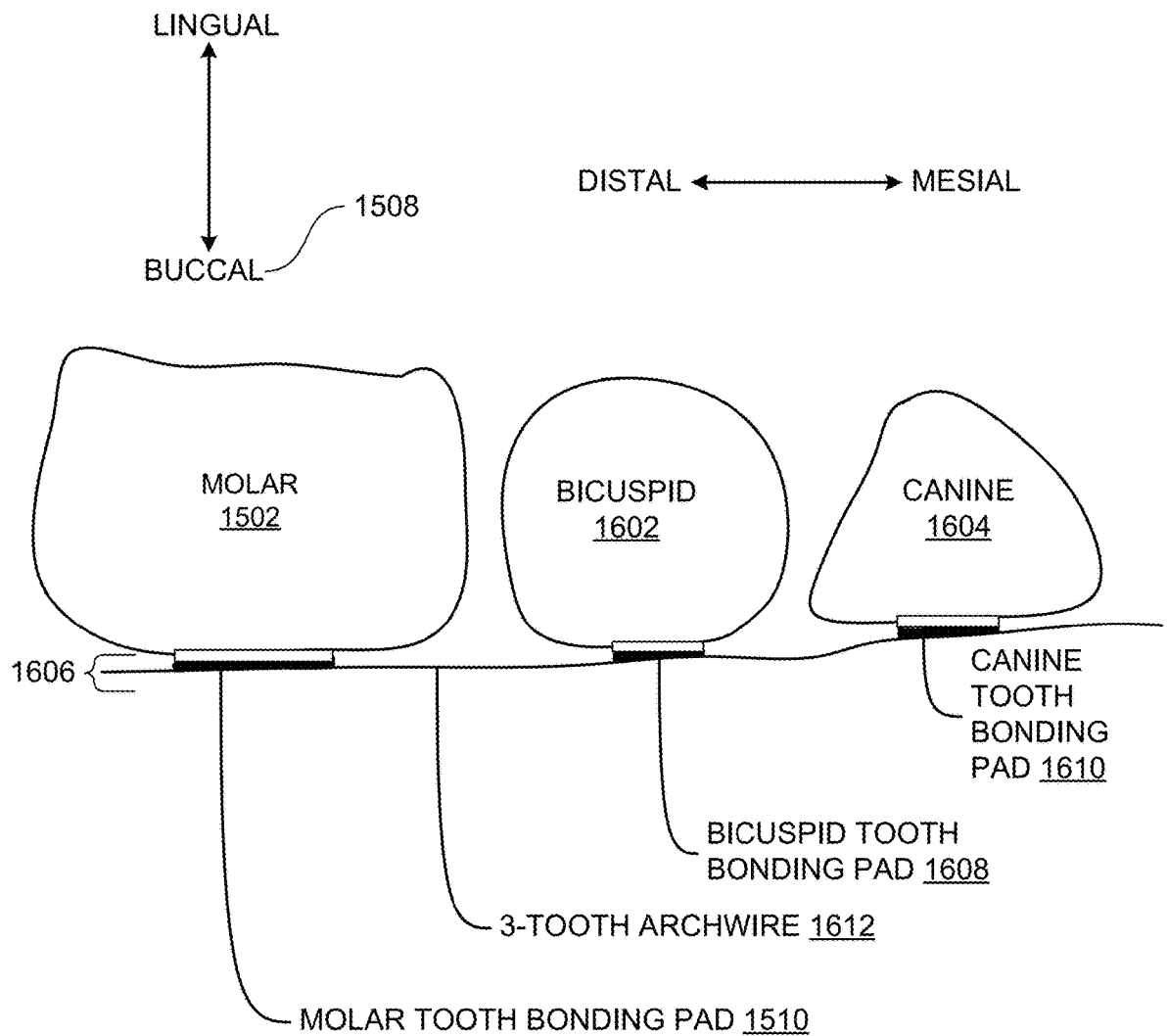
FIG. 16 is an occlusal-view block diagram of a carbon-nanotube tooth-bonding apparatus applied to a molar tooth, a bicuspid tooth and a canine tooth, according to an implementation.

FIG. 16 is an occlusal-view block diagram of a carbon-nanotube tooth-bonding apparatus 1600 applied to a molar tooth, a bicuspid tooth and a canine tooth, according to an implementation. FIG. 16 shows a molar tooth 1502, a bicuspid tooth 1602 and a canine tooth 1604. A carbon-nanotube tooth-bonding apparatus 1606 includes a molar tooth bonding pad 1510 that is removeably attached to the buccal surface 1508 of the molar tooth 1502. The carbon-nanotube tooth-bonding apparatus 1606 includes a bicuspid tooth bonding pad 1608 that is removeably attached to the buccal surface 1508 of the bicuspid tooth 1602. The carbon-nanotube tooth-bonding apparatus 1606 includes a canine tooth bonding pad 1610 that is removeably attached to the buccal surface 1508 of the canine tooth 1604.

A three-tooth segment of archwire 1612 of the carbon-nanotube tooth-bonding apparatus 1606 is attached to the molar tooth bonding pad 1510, the bicuspid tooth bonding pad 1608 and the canine tooth bonding pad 1610.

Apparatus 500, apparatus 600, apparatus 700, apparatus 900, apparatus 1100 and apparatus 1300 are implementations of the carbon-nanotube tooth-bonding apparatus 1606. The carbon-nanotube tooth-bonding apparatus 1606 does not have or include an orthodontic bracket, which as a result of the absent orthordontic bracket the carbon-nanotube tooth-bonding apparatus 1606 can be fabricated easily, simply and inexpensively, and the carbon-nanotube tooth-bonding apparatus 1606 has a low physical profile and a smaller height dimension that positions the archwire further away from the inside of the cheek of the patient, thus reducing friction of the inside of the cheek on the archwire, and thus improving comfort of the patient.

Apparatus 500, apparatus 600, apparatus 700, apparatus 900, apparatus 1100 and apparatus 1300 are implementations of the carbon-nanotube tooth-bonding apparatus 1606. The carbon-nanotube tooth-bonding apparatus 1606 does not have or include an orthodontic bracket, which as a result of the absent orthordontic bracket, the carbon-nanotube tooth-bonding apparatus 1606 can be fabricated easily, simply and inexpensively, and the carbon-nanotube tooth-bonding apparatus 1606 has a low physical profile and a smaller height dimension that positions the archwire further away from the inside of the cheek of a patient to which the carbon-nanotube tooth-bonding apparatus 1606 is applied, thus reducing friction of the inside of the cheek on the archwire 1606, and thus improving comfort of the patient to which the carbon-nanotube tooth-bonding apparatus 1606 is applied.

The dimensions and sizes of apparatus shown in FIG. 5, FIG. 6, FIG. 8, FIG. 15, and FIG. 16 are not exemplary or limiting.

Figure 17:
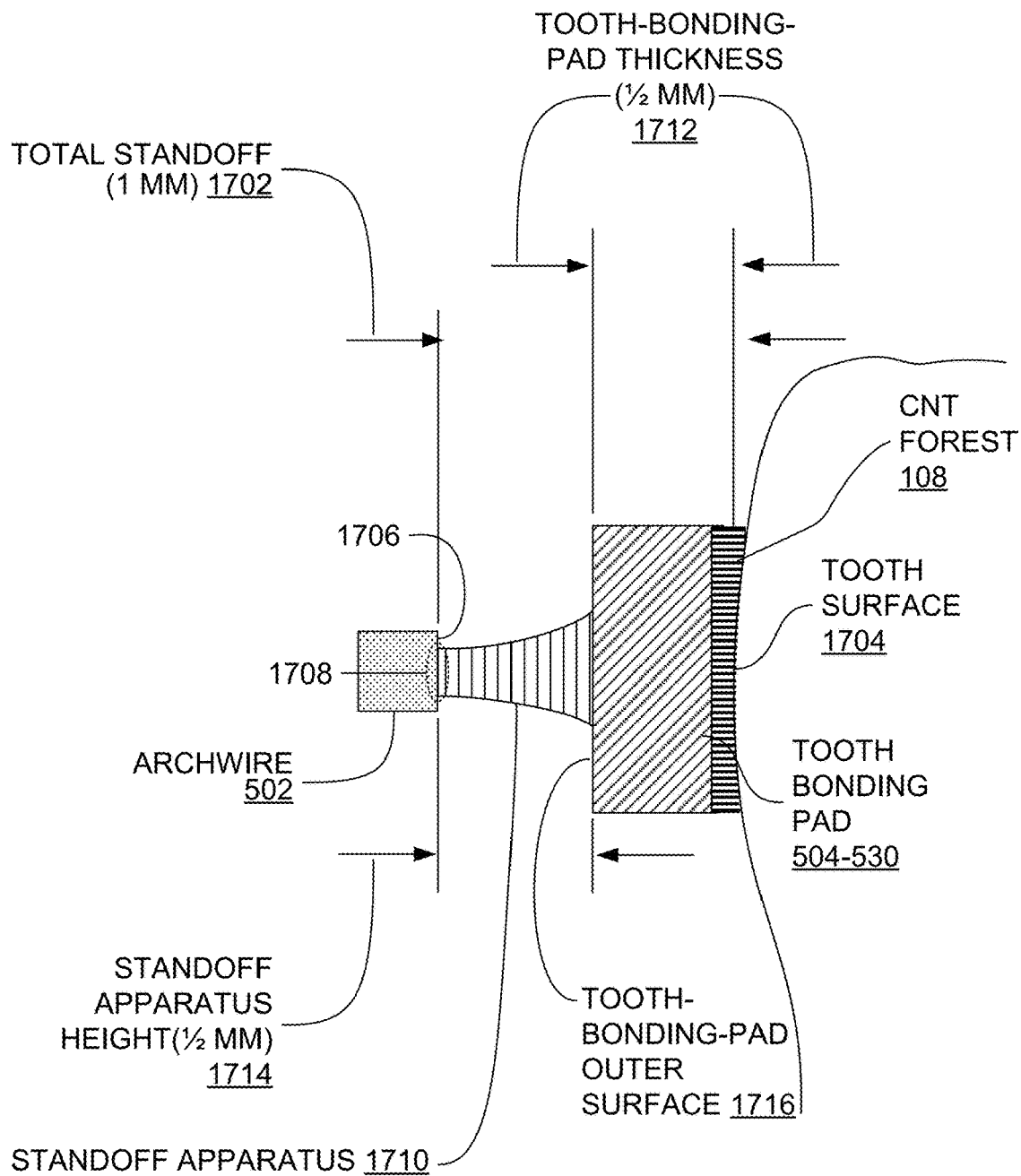
FIG. 17 is a side-view block diagram of a carbon-nanotube tooth-bonding apparatus applied to a bicuspid tooth, according to an implementation having a short stand-off apparatus.

FIG. 17 is a side-view block diagram of a carbon-nanotube tooth-bonding apparatus 1700, according to an implementation having a short stand-off apparatus. A total standoff 1702 of a carbon-nanotube tooth-bonding apparatus is the distance between the surface of the tooth 1704 and the inner surface 1706 of the archwire 502 at the attachment area 1708 between the archwire and a standoff apparatus 1710. In the implementation shown in FIG. 17, the total standoff 1702 distance is 1 mm. The total standoff 1702 comprises two components: (1) the thickness 1712 of the bonding pad 504-530 and (2) the distance 1714 between the outer surface 1716 of the carbon-nanotube bonding substrate 504-530 and where the archwire 502 is attached to the inner surface 1706 of the attachment area 1708. The total standoff 1702 is simply the sum of (1) and (2) above. In the implementation shown in FIG. 17, the total standoff 1702 of 1 mm is the sum of the ½ mm thickness 1712 of the bonding pad 504-530 and the ½ mm distance 1714 between the outer surface 1716 of the bonding pad 504-530 where the archwire 502 is attached to the inner surface 1706 of the attachment area 1708.

The distance 1714 is also known as the "bonding pad offset". In some applications of the carbon-nanotube bonding substrate/apparatus, the desired result benefits from, or be enhanced by the bonding pad offset 1714 created by the standoff apparatus 1710. The applications which benefit from the bonding pad offset 1714 created by the standoff apparatus 1710 include treatment of relapse of previous orthodontic treatment, which in some instances have no bonding pad offset 1714 (0 mm) and no standoff apparatus 1710 at the canines and molars, and between ½ mm and 2 mm of offset at the incisors and bicuspids. For this application, the larger values of bonding pad offset 1714 can be associated with the lower incisors, the mid range values of offset with the upper incisors, and the smaller values with the bicuspids. Particular formulations or prescriptions for offset values should not be considered as limiting the claims nor the scope of this disclosure.

Figure 18:
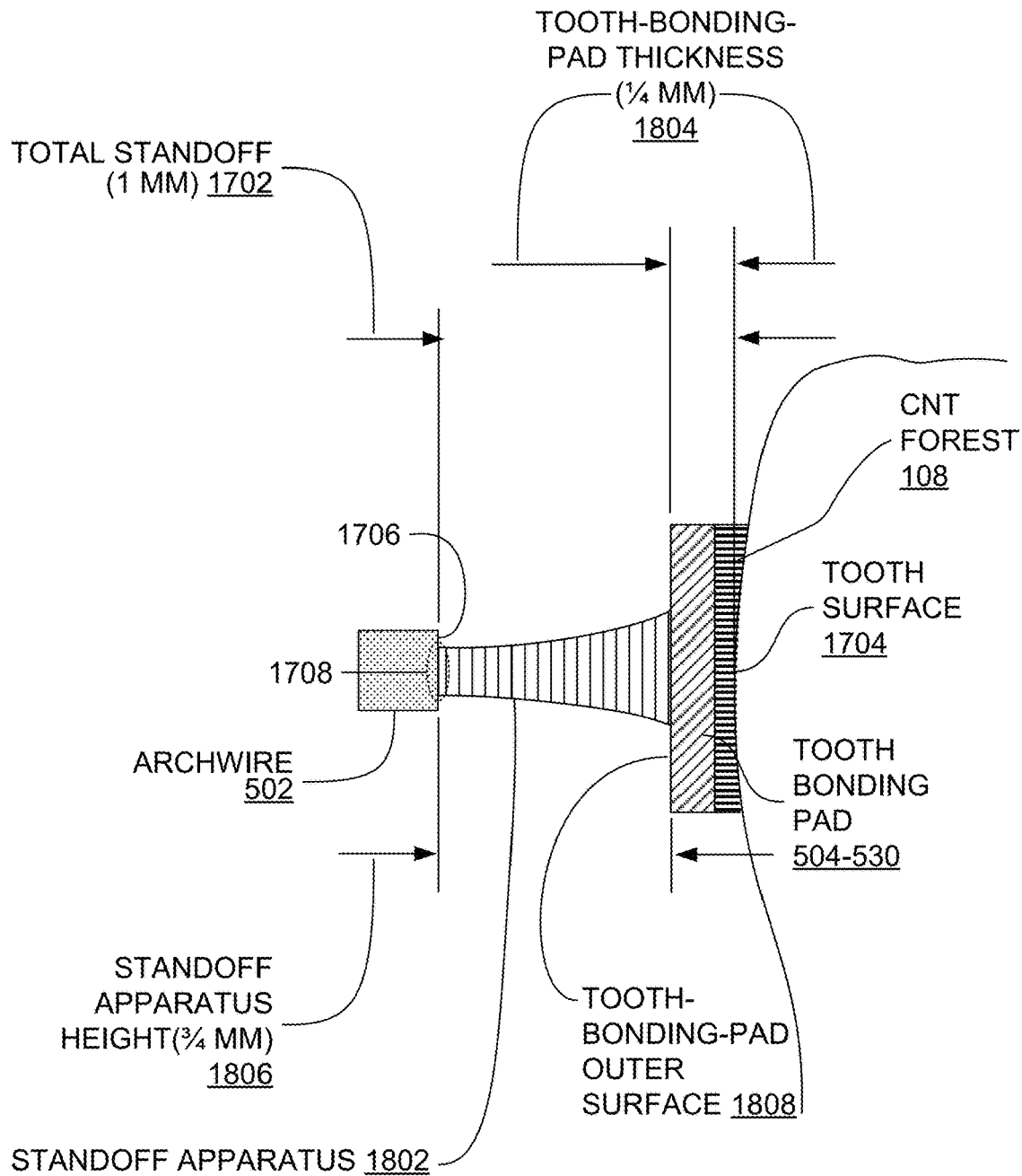
FIG. 18 is a side-view block diagram of a carbon-nanotube tooth-bonding apparatus applied to a bicuspid tooth, according to an implementation having a long stand-off apparatus.

FIG. 18 is a side-view block diagram of a carbon-nanotube tooth-bonding apparatus 1800, according to an implementation having a long standoff apparatus. A total standoff 1702 of a carbon-nanotube tooth-bonding apparatus is the distance between the surface of the tooth 1704 and the inner surface 1706 of the archwire 502 at the attachment area 1708 between the archwire and a standoff apparatus 1802. In the implementation shown in FIG. 17, the total standoff 1702 distance is 1 mm. The total standoff 1702 comprises two components: (1) the thickness 1804 of the bonding pad 504-530 and (2) the distance 1806 between the outer surface 1808 of the carbon-nanotube bonding substrate 504-530 and where the archwire 502 is attached to the inner surface 1706 of the attachment area 1708. The total standoff 1702 is simply the sum of (1) and (2) above. In the implementation shown in FIG. 18, the total standoff 1702 of 1 mm is the sum of the ⅔ mm thickness 1804 of the bonding pad 504-530 and the 34 mm distance 1806 between the outer surface 1808 of the bonding pad 504-530 where the archwire 502 is attached to the inner surface 1706 of the attachment area 1708.

Figure 19:
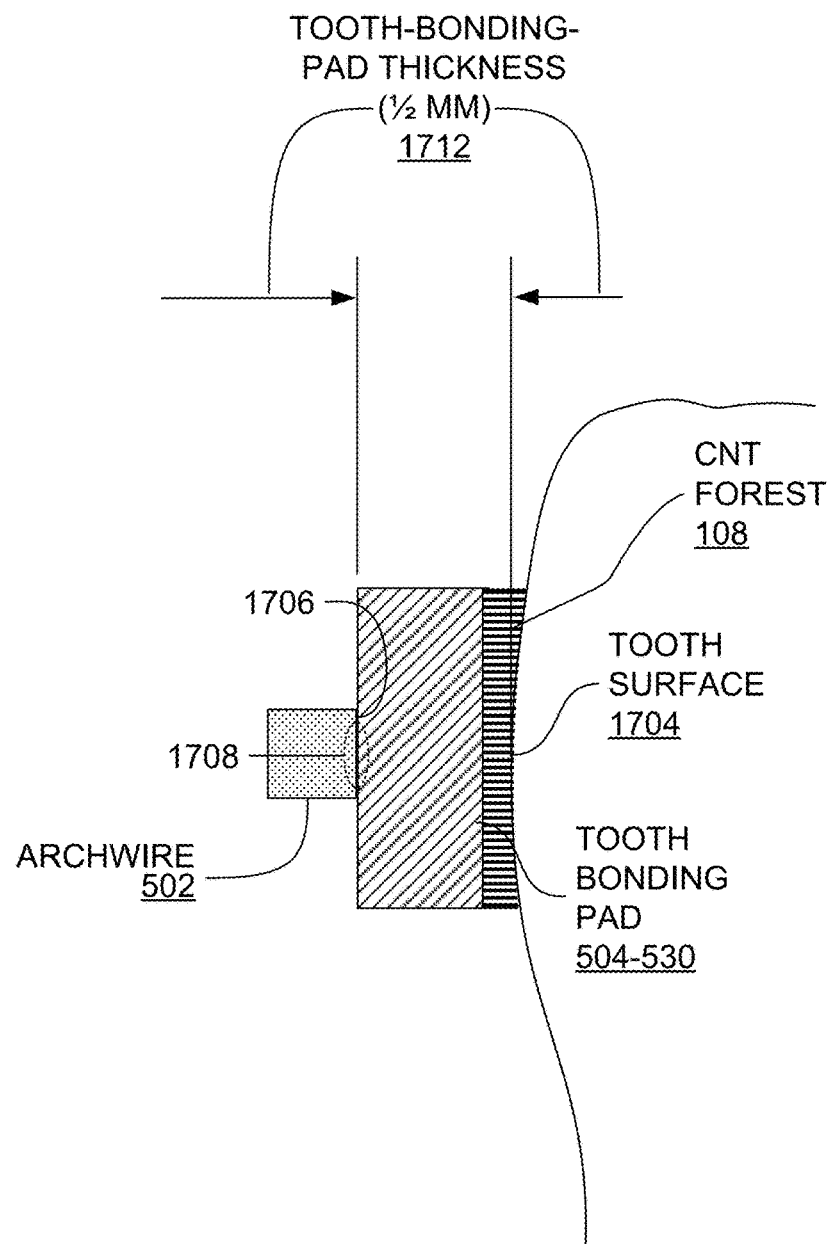
FIG. 19 is a side-view block diagram of a carbon-nanotube tooth-bonding apparatus, according to an implementation having no standoff apparatus.

FIG. 19 is a side-view block diagram of a carbon-nanotube tooth-bonding apparatus 1900, according to an implementation having no standoff apparatus. A total standoff of the carbon-nanotube tooth-bonding apparatus is the distance between the surface of the tooth 1704 and the inner surface 1706 of the archwire 502 at the attachment area 1708 between the archwire 502 and the surface of the tooth 1704. In the implementation shown in FIG. 19, the total standoff distance is ½ mm. The total standoff comprises one component: (1) the thickness 1712 of the bonding pad 504-530.

Figure 20:
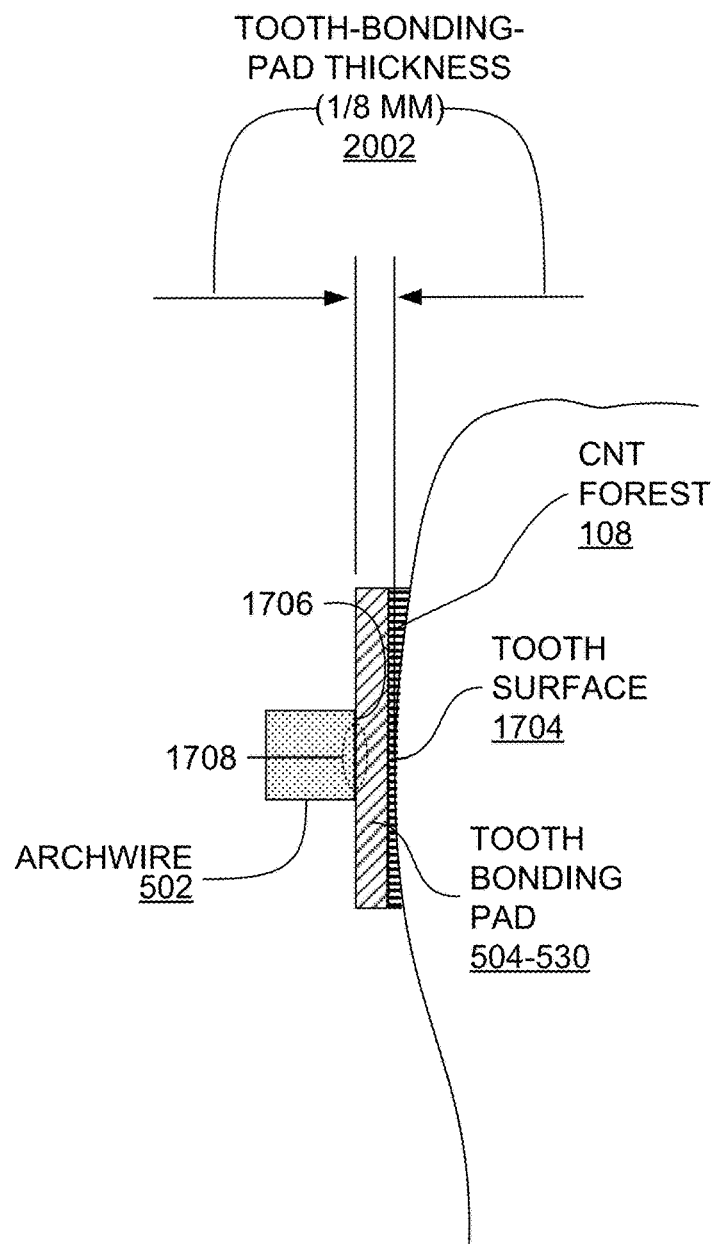
FIG. 20 is a side-view block diagram of a carbon-nanotube tooth-bonding apparatus, according to an implementation having no standoff apparatus.

FIG. 20 is a side-view block diagram of a carbon-nanotube tooth-bonding apparatus 2000, according to an implementation having no standoff apparatus. A total standoff of the carbon-nanotube tooth-bonding apparatus is the distance between the surface of the tooth 1704 and the inner surface 1706 of the archwire 502 at the attachment area 1708 between the archwire 502 and the surface of the tooth 1704. In the implementation shown in FIG. 20, the total standoff distance is ½ mm. The total standoff comprises one component: (1) the thickness 2002 of the bonding pad 504-530.

FIG. 21 is a table 2100 of spacing between carbon-nanotube bonding substrates in an upper archwire for a human, according to an implementation. An upper archwire is an archwire that is applied to the upper teeth in a human mouth. The spacing dimensions are between the centers of the carbon-nanotube bonding substrates, such as shown in FIG. 6. Table 2100 illustrates the spacing dimensions between the centers of carbon-nanotube bonding substrates of a number of different upper archwires, Archwire #1 (2002), Archwire #2 (2004), Archwire #3 (2006), Archwire #4 (2008) and Archwire #5 (2010). Table 2100 illustrates the spacing dimensions of the five different upper archwires (2002-2010) between the centers of carbon-nanotube bonding substrates for spaces "ML-1" 2112, "Space 1-2" 2114, "Space 2-3" 2116, "Space 3-4" 2118, "Space 4-5" 2120 "Space 5-6" 2122 and "Space 6-7" 2124. Table 2100 discloses that the spacing "Space 5-6" (608 and 632 in FIG. 6) between the centers of carbon-nanotube bonding substrates 506 and 508, and carbon-nanotube bonding substrates 526 and 528, respectively, for Archwire #2 is 7.8 mm.

FIG. 22 is a table 2200 of spacing between carbon-nanotube bonding substrates in a lower archwire for a human, according to an implementation. A lower archwire is an archwire that is applied to the lower teeth in a human mouth. The spacing dimensions are between the centers of the carbon-nanotube bonding substrates, such as shown in FIG. 6. Table 2200 illustrates the spacing dimensions between the centers of carbon-nanotube bonding substrates of a number of different lower archwires, Archwire #1 (2102), Archwire #2 (2104), Archwire #3 (2106), Archwire #4 (2108) and Archwire #5 (2110). Table 2200 illustrates the spacing dimensions of the five different lower archwires (2102-2110) between the centers of carbon-nanotube bonding substrates for spaces "ML-1" 2212, "Space 1-2" 2214, "Space 2-3" 2216, "Space 3-4" 2218, "Space 4-5" 2220 "Space 5-6" 2222 and "Space 6-7" 2224. Table 2200 discloses that the spacing "Space 1-2" (616 and 624 in FIG. 6) between the centers of carbon-nanotube bonding substrates 514 and 516, and carbon-nanotube bonding substrates 518 and 520, respectively, for Archwire #1 is 4.4 mm.

Method Implementations

In the previous section, implementations of apparatus are described. In this section, particular methods of such those implementations are described by reference to a series of flowcharts.

Figure 23:
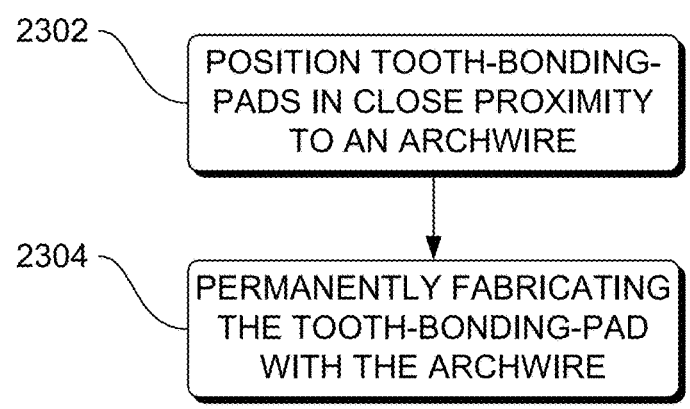
FIG. 23 is a flowchart of a method to fabricate a carbon-nanotube tooth-bonding apparatus according to an implementation.

FIG. 23 is a flowchart of a method 2300 to fabricate a carbon-nanotube tooth-bonding apparatus, according to an implementation. In method 2300, at least one carbon-nanotube bonding substrate and an archwire are transformed into a carbon-nanotube tooth-bonding apparatus, such as apparatus 500, apparatus 600, apparatus 700, apparatus 900, apparatus 1100 and apparatus 1300.

Method 2300 includes positioning one or more carbon-nanotube bonding substrates in close proximity to an archwire at fixed positions of the archwire, at block 2302. One example of the carbon-nanotube bonding substrates are carbon-nanotube bonding substrates 504-530 in FIG. 5. One example of the archwire is archwire 502 in FIG. 5.

Method 2300 includes permanently fabricating the one or more carbon-nanotube bonding substrates with the archwire at fixed positions of the archwire, at block 2304.

In one implementation of permanently fabricating 2304 one or more carbon-nanotube bonding substrates with the archwire at fixed positions of the archwire, each of the plurality of carbon-nanotube bonding substrates is metallurgically permanently fabricated into the archwire at fixed positions of the archwire.

In one implementation of permanently fabricating one or more carbon-nanotube bonding substrates with an archwire at fixed positions of the archwire, at block 2304, each of the plurality of carbon-nanotube bonding substrates (e.g. 504-530 in FIG. 5) are formed as one complete integral unit with the archwire (e.g. 502 in FIG. 5). Forming the carbon-nanotube bonding substrates as one complete integral unit with the archwire is performed in one implementation by casting or vacuum casting a melted metal into molds of magnesia and silica by a dental argon-arc pressure casting machine with a copper crucible, or by an argon arc centrifugal casting machine, or by an arc-melting gas pressure casting machine. One example of a dental argon-arc pressure casting machine is the AX-AWM1 dental argon-arc pressure casting machine manufactured by Tianjin Aixin Medical Equipment Co., Ltd in Tainjin, China 300308. One example of an argon arc centrifugal casting machine is an argon arc centrifugal casting machine manufactured by O'Hara Co., Ltd of Osaka, Japan. One example of an arc-melting gas pressure casting machine is the AX-AWMAX1 arc-melting gas pressure casting machine manufactured by Tianjin Aixin Medical Equipment Co., Ltd in Tainjin, China 300308.

In one implementation of permanently fabricating one or more carbon-nanotube bonding substrates with the archwire at fixed positions of the archwire at block 2304, each of the plurality of carbon-nanotube bonding substrates (e.g. 504-530 in FIG. 5) are permanently fabricated to the archwire (e.g. archwire 502 in FIG. 5) through a welding/brazing process that is appropriate for the materials of the archwire and the carbon-nanotube bonding substrate(s). For example the carbon-nanotube bonding substrates are permanently fabricated to the archwire by sintering, laser welding, electrical resistance welding, tungsten inert gas welding or brazing/soldering. In some implementations of laser welding, crystals of yttrium, aluminum, garnet and neodymium emit laser beams. In some implementations of laser welding, gold alloys are laser welded to a cobalt-chromium alloy. In some implementations of tungsten inert gas welding, welding heat is produced by a light bow between tungsten anode and metal. In some implementations of brazing/soldering, the brazing/soldering is performed at more than 450 degrees C.

In one implementation of permanently fabricating one or more carbon-nanotube bonding substrates with the archwire at fixed positions of the archwire, each of the plurality of carbon-nanotube bonding substrates (e.g. 504-530 in FIG. 5) are permanently fabricated to the archwire (e.g. archwire 502 in FIG. 5) by welding.

In one implementation of permanently fabricating one or more carbon-nanotube bonding substrates with the archwire at fixed positions of the archwire, at block 2304, each of the plurality of carbon-nanotube bonding substrates is glued onto the archwire at fixed positions of the archwire.

In one implementation of permanently fabricating 2304 one or more carbon-nanotube bonding substrates at fixed positions of the archwire, each of the plurality of carbon-nanotube bonding substrates is crimped onto the archwire at fixed positions of the archwire.

Figure 24:
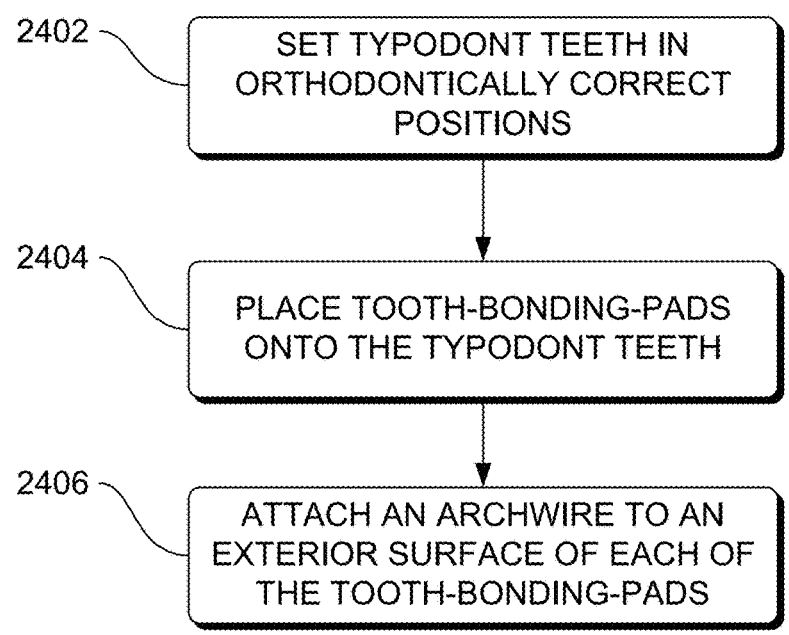
FIG. 24 is a flowchart of a method to fabricate a carbon-nanotube tooth-bonding apparatus according to an implementation.

FIG. 24 is a flowchart of a method 2400 to fabricate a carbon-nanotube tooth-bonding apparatus, according to an implementation. In method 2400, at least one carbon-nanotube bonding substrate and an archwire are transformed into a carbon-nanotube tooth-bonding apparatus, such as apparatus 500, apparatus 600, apparatus 700, apparatus 900, apparatus 1100 and apparatus 1300.

Method 2400 includes setting anatomically correct typodont teeth in orthodontically correct positions, at block 2402. Thereafter, anatomically contoured carbon-nanotube bonding substrates are placed onto labial or buccal surfaces of the typodont teeth in the occlusal-gingival center and mesial-distal center of the labial and buccal surface of orthodontically correct positions, at block 2404.

Method 2400 also includes attaching the archwire in an occlusal plane, passively contacting an exterior surface of each of the plurality of carbon-nanotube bonding substrates, and rigidly attaching the archwire to a midpoint of each of the corresponding plurality of carbon-nanotube bonding substrates, at block 2406.

Figure 25:
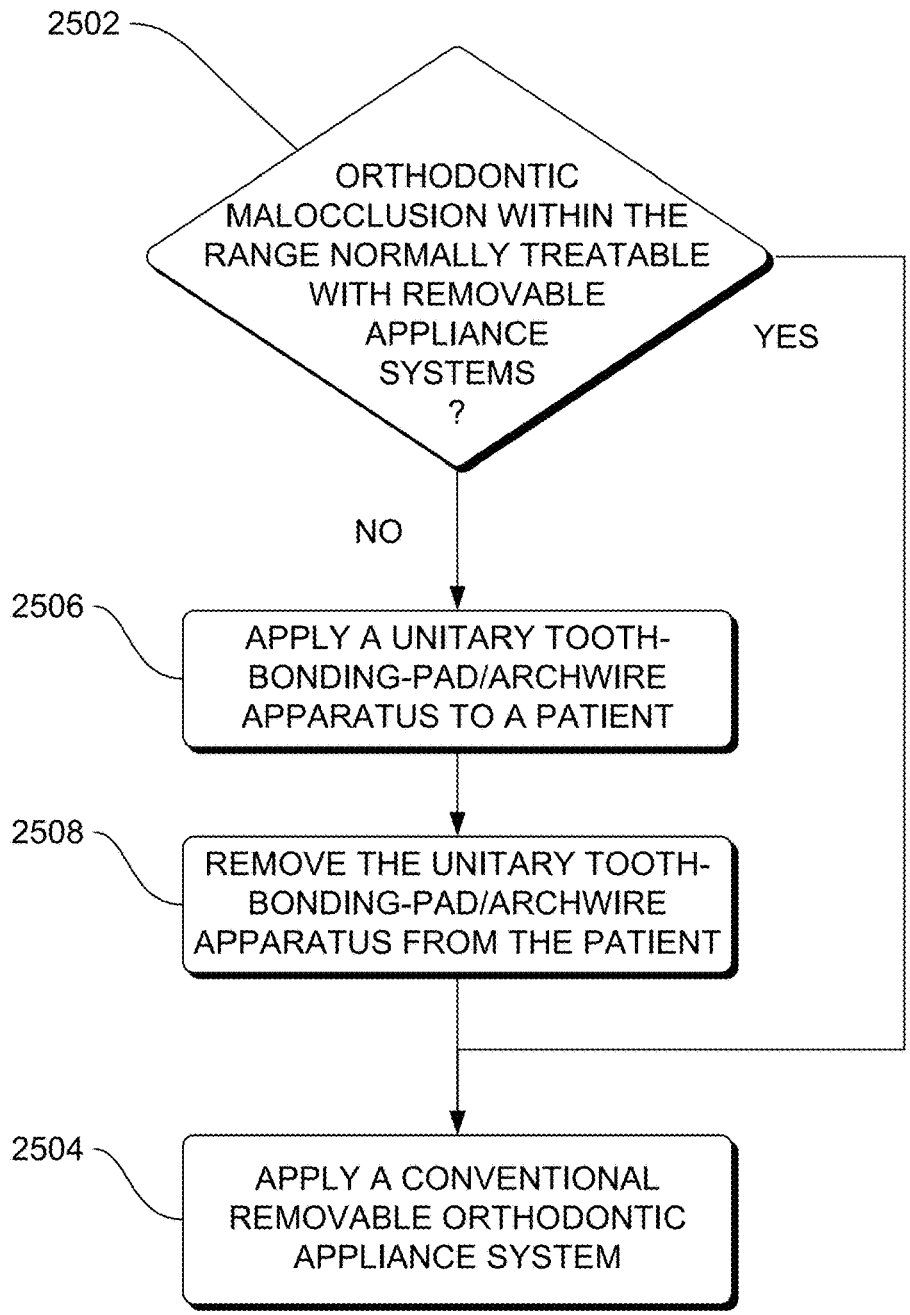
FIG. 25 is a flowchart of a method to implement a carbon-nanotube tooth-bonding apparatus, according to an implementation before application of removable orthodontic appliance systems.

FIG. 25 is a flowchart of a method 2500 to implement a carbon-nanotube tooth-bonding apparatus, according to an implementation before application of removable orthodontic appliance systems. Method 2500 provides effective treatment for orthodontic patients who are not originally practical candidates for removable orthodontic appliance systems.

At block 2502, if orthodontic malocclusion that is within the range that is conventionally diagnosed as treatable with removable applicant systems, then conventional treatment such as applying a conventional removable orthodontic appliance system to treat the malocclusion is performed at block 2504. However, if orthodontic malocclusion is outside of the range that is conventionally diagnosed as treatable with removable applicant systems, then at block 2506 in method 2500, an appropriately selected implementation of apparatus 500 is applied to a patient as an enabling appliance for orthodontic patients who, without prior treatment using apparatus 500, would not be practical candidates for complete and finishing orthodontic treatment with other removable orthodontic appliance systems. The appropriate implementation of apparatus 500 is based in part on the implementation variations described in FIG. 21 and FIG. 22. Some orthodontic patients who are not practical candidates for removable orthodontic appliance systems have less severe dental malocclusions and/or relapse of prior complete orthodontic treatment. Specifically, there are many cases of orthodontic malocclusion which cannot be fully treated with Invisalign® removable teeth aligner appliances alone. A significant number of patients having dental malocclusion can brought into the treatment range of Invisalign® removable teeth aligner appliances with a prior short-term application of apparatus 500. Additionally, many cases of malocclusion which are already treatable with Invisalign® removable teeth aligner appliances can be properly prepared for express treatment using Invisalign® removable teeth aligner appliances at a significantly overall reduced cost, and with less wear time by the patient.

After the application of apparatus 500 has achieved results that improve the prognosis for application of removable orthodontic appliance systems, apparatus 500 is removed from the patient, at block 2508, and then a conventional removable orthodontic realigner-retainer appliance system is applied to the patient, at block 2504.

FIG. 26 is a flowchart of a method 2600 to implement a carbon-nanotube tooth-bonding apparatus, to correct orthodontic relapse. Method 2600 provides effective treatment for orthodontic patients whose prior orthodontic treatment has relapsed or regressed.

If orthodontic relapse is not diagnosed, at block 2602, then conventional post-treatment retention is performed. However orthodontic relapse is diagnosed at block 2602, because the degree of relapse is outside the range of treatment of a conventional realigner-retainer appliance, an appropriately selected implementation of apparatus 500 is applied to the relapsed arches of the patient to bring the degree of orthodontic correction back within range of a realigner or a retainer, at block 2506. The appropriate implementation of apparatus 500 is based in part on the implementation variations described in FIG. 18 and FIG. 22.

After the application of apparatus 500 has achieved results that improve the prognosis for application of removable orthodontic appliance systems, apparatus 500 is removed from the patient, at block 2508, and the conventional orthodontic realigner/retainer appliance system is applied to the patient, at block 2606.

Figure 27:
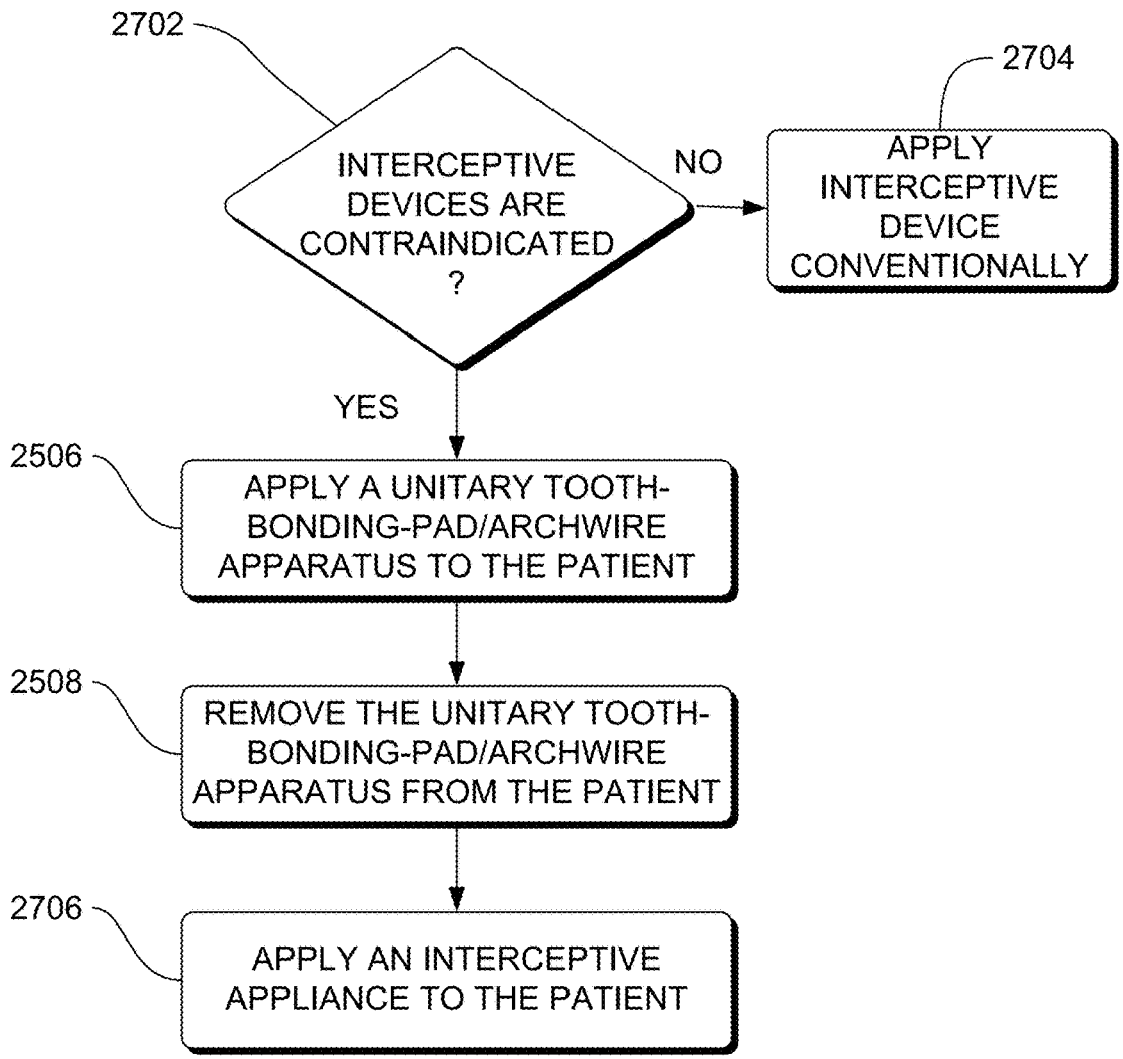
FIG. 27 is a flowchart of a method to implement a carbon-nanotube tooth-bonding apparatus, to facilitate the application of interceptive removable orthodontic devices on patients who are in a mixed dentition age range.

FIG. 27 is a flowchart of a method 2700 to implement a carbon-nanotube tooth-bonding apparatus, to facilitate the application of interceptive removable orthodontic devices on patients who are in a mixed dentition age range. Patients who are in a mixed dentition age range have one or more teeth are positioned such that the implementation of interceptive devices are be contraindicated, these problematically positioned teeth can be moved into positions by apparatus 500 to the extent that the new positions permit the implementation of these interceptive appliances.

When considering the use of a conventional interceptive orthodontic appliance for patients in the age range of mixed dentition if one or more malpositioned teeth contraindicate the use of conventional interceptive orthodontic appliances at block 2702, apparatus 500 can be applied to the patient, at block 2506, to bring the malpositioned teeth into positions that permit the use of the conventional interceptive orthodontic appliance on the patient. If the patient has no malpositioned teeth that contraindicat the use of the conventional interceptive orthodontic appliance, then the conventional interceptive orthodontic appliance is applied in a conventional manner, at block 2704.

After the application of apparatus 500 has achieved results that improve the prognosis for application of interceptive appliances, apparatus 500 is removed from the patient, at block 2508, and the interceptive appliance is applied to the patient, at block 2706.

Interceptive orthodontic appliances include Frankel orthodontic appliances, Schwarz orthodontic appliances and Bionator orthodontic appliances. Method 2700 provides effective treatment for orthodontic patients who are in a mixed dentition age range.

Figure 28:
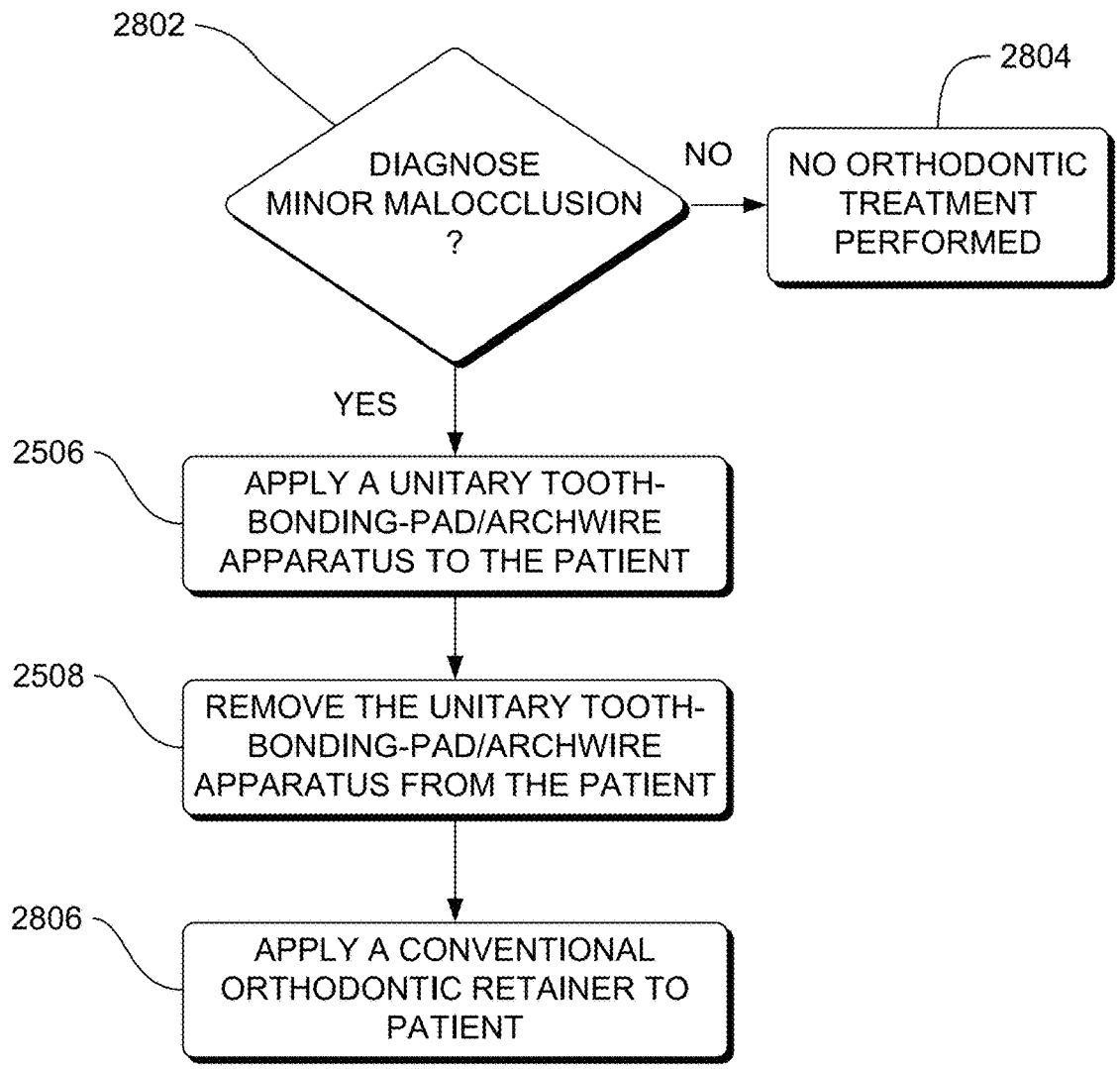
FIG. 28 is a flowchart of a method to implement a carbon-nanotube tooth-bonding apparatus, to correct a minor orthodontic malocclusion.

FIG. 28 is a flowchart of a method 2800 to implement a carbon-nanotube tooth-bonding apparatus, to correct a minor orthodontic malocclusion. Method 2800 provides effective treatment for orthodontic patients having a minor orthodontic malocclusion.

In method 2800, if a minor malocclusion in one or more arches is not diagnosed at block 2802, then no orthodontic treatment is performed at block 2804. However, if a minor malocclusion in one or more arches is diagnosed, at block 2802, in response to diagnosis of the minor orthodontic malocclusion, apparatus 500 is applied to the patient, at block 2506, to correct the minor orthodontic malocclusion. An example of a minor orthodontic malocclusion is a dental malocclusion that includes only minor tooth displacements, such as buccal-lingual displacements, rotations, tipping, and/or vertical height discrepancies.

After the application of apparatus 500 has corrected the minor orthodontic malocclusion, apparatus 500 is removed from the patient, at block 2508.

In some implementations, following completion of orthodontic treatment involving apparatus 500, any conventional orthodontic retainer, such as a Hawley orthodontic appliance, is applied to the patient at block 2806 to retain the orthodontic result.

Figure 29:
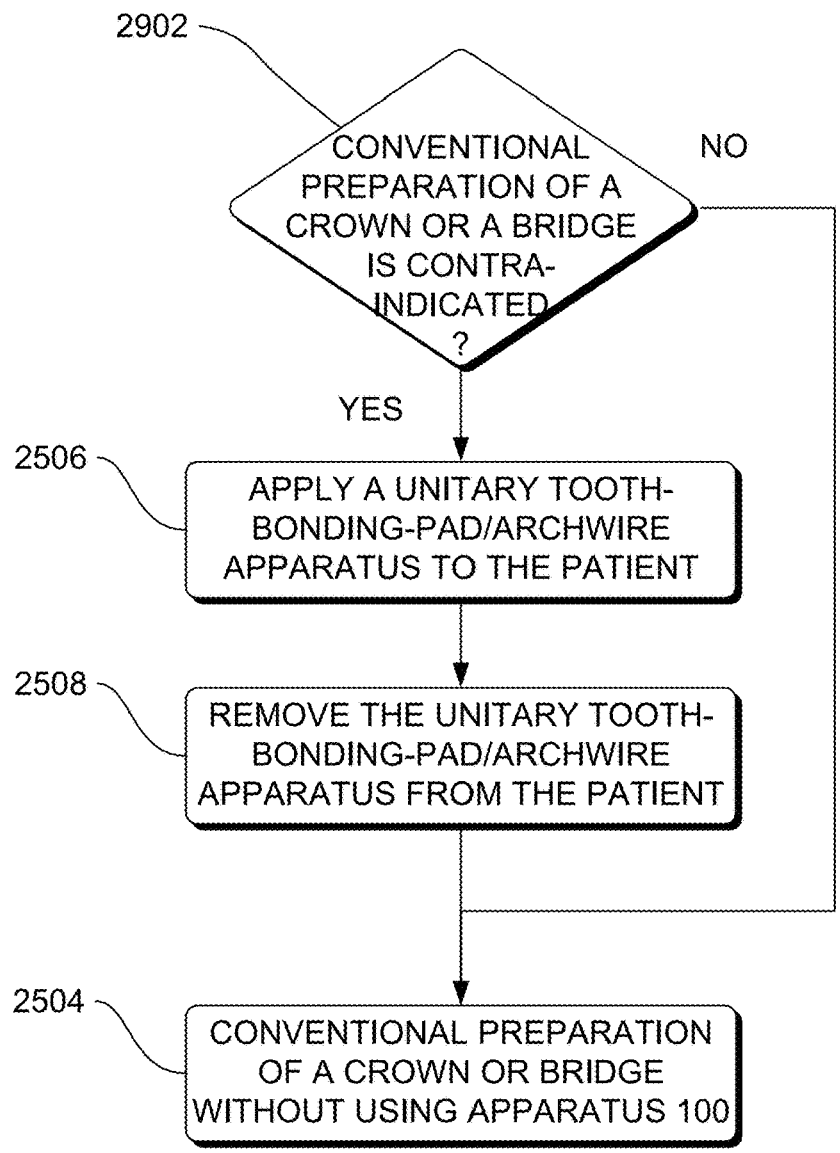
FIG. 29 is a flowchart of a method to implement a carbon-nanotube tooth-bonding apparatus, in coordination with application of crowns and abutments.

FIG. 29 is a flowchart of a method 2900 to implement a carbon-nanotube tooth-bonding apparatus, in coordination with application of crowns and abutments.

Apparatus 500 can be implemented prior to crown and bridge work in dentistry. When one or more of teeth that are to be prepared for crowns or as abutments for bridgework are in less than ideal positions, apparatus 500 can be implemented to better position these teeth for stress bearing associated with chewing forces, and also to allow for a more aesthetically appearing cosmetic result. For example, for teeth which are tipped or displaced from ideal positions of the teeth, orthodontic correction toward ideal positions of the teeth would permit the forces of mastication to be correctly directed along the long axis of the tooth, instead of producing periodontally unhealthy excessive lateral force components. Also, when anterior crowns are applied, significant labial-lingual misalignment can often be greater than can be compensated by selective tooth reduction alone. When the labial-lingual misalignment is greater than can be compensated by selective tooth reduction alone, short term correction involving apparatus 500 aligns the anterior teeth so that conservative crown preparation will allow for a cosmetically ideal result.

If conventional preparation of a crown or a bridge is not contra-indicated because of tooth misalignment, at block 2902, the conventional preparation of a crown or bridge without using apparatus 500 is performed, at block 2904. However, if conventional preparation of a crown or a bridge is contra-indicated because of tooth misalignment, at block 2902, then an appropriately selected implementation of apparatus 500 is applied to the patient to better position the teeth for stress bearing associated with chewing force, at block 2506.

After the application of apparatus 500 has achieved results that improve the prognosis for application of crowns and/or bridges, apparatus 500 is removed from the patient and the tooth or teeth are conventionally prepared for an ideal crown or bridge result and a temporary crown or bridge coverage is applied based on conventional techniques, at block 2508, and conventional preparation of a crown or bridge without using apparatus 500 is performed, at block 2904.

The methods disclosed herein do not include attaching or including a bracket to the apparatus.

Conclusion

A nanotube bonding substrate/archwire system that does not include an orthodontic bracket is described herein.

In one implementation, a plurality of orthodontic archwires each have tooth bonding pads attached in specified locations. Five archwires of standardized archform geometry for the maxillary arch for each specified diameter or cross-section, and five archwires of standardized archform geometry for the mandibular arch for each specified diameter or cross section. As there are four specified diameters or cross-sections of archwires for each of the five standardized archform geometries, a total of twenty archwires can be fabricated for the upper arch, and a total of twenty archwires can be fabricated for the lower arch. Each archwire has a dental midline marking.

Although specific implementations are illustrated and described herein, it will be appreciated by those of ordinary skill in the art that any arrangement which is calculated to achieve the same purpose may be substituted for the specific implementations shown. This disclosure is intended to cover any adaptations or variations. For example, one of ordinary skill in the art will appreciate that implementations can be made in any material or any other process that provides the required function.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices can be introduced without departing from the scope of implementations. One of skill in the art will readily recognize that implementations are applicable to new archwires and different carbon-nanotube bonding substrates.

The terminology in this disclosure is meant to include all archwires and tooth-bonding pads and alternate technologies which provide the same functionality as described herein.

In some aspects, an apparatus consists of an archwire and a plurality of carbon-nanotube bonding substrates in which each of the plurality of carbon-nanotube bonding substrates are permanently fabricated to the archwire at fixed positions of the archwire. In some implementations, each of the plurality of carbon-nanotube bonding substrates that is permanently fabricated to the archwire includes at least one of the plurality of carbon-nanotube bonding substrates that are formed as one complete integral unit with the archwire. In some implementations, each of the plurality of carbon-nanotube bonding substrates that is permanently fabricated to the archwire includes at least one of the plurality of carbon-nanotube bonding substrates being permanently fabricated to the archwire through a welding/brazing method that is appropriate for the materials of the archwire and the carbon-nanotube bonding substrate. In some implementations, each of the plurality of carbon-nanotube bonding substrates that is permanently fabricated to the archwire includes at least one of the plurality of carbon-nanotube bonding substrates being welded to the archwire. In some implementations, each of the plurality of carbon-nanotube bonding substrates that is permanently fabricated to the archwire at fixed positions of the archwire includes at least one of the plurality of carbon-nanotube bonding substrates being metallurgically permanently fabricated to the archwire at fixed positions of the archwire. In some implementations, each of the plurality of carbon-nanotube bonding substrates that is permanently fabricated to the archwire at fixed positions of the archwire includes at least one of the plurality of carbon-nanotube bonding substrates are glued to the archwire at fixed positions of the archwire. In some implementations, the plurality of carbon-nanotube bonding substrates are 14 carbon-nanotube bonding substrates. In some implementations, each of the carbon-nanotube bonding substrates have an orientation to the archwire such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In some implementations, the orientation of each of the carbon-nanotube bonding substrates include appositioning the carbon-nanotube bonding substrates with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the carbon-nanotube bonding substrates onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, each of the carbon-nanotube bonding substrates include at least one contour of each of the carbon-nanotube bonding substrates is produced from existing statistical norms of the labial and buccal surfaces of human teeth. In some implementations, each of the carbon-nanotube bonding substrates include an occlusal-gingival height in a range of 1.5 mm to 4 mm and a mesial-distal length in a range of 1.5 mm to 3.0 mm. In some implementations, the archwire includes thermally activated nickel-titanium (NiTi) metal. In some implementations, the thermally activated nickel-titanium (NiTi) metal includes force activation occurring at a temperature of approximately 27 degrees Celsius. In some implementations, the archwire includes a diameter selected from the group of diameters consisting of 0.012 inches in diameter round, 0.014 inches in diameter round, 0.016 inches in diameter round, and 0.016×0.016 inches rectangular cross section. In some implementations, the archwire includes a tooth-color as a result of manufacturing with epoxy coatings or other tooth-colored surfaces. In some implementations, the at least one of the plurality of carbon-nanotube bonding substrates includes a tooth-color as a result of manufacturing with epoxy coatings or other tooth-colored surfaces. In some implementations, each of the plurality of carbon-nanotube bonding substrates that is permanently fabricated to the archwire includes each of the plurality of carbon-nanotube bonding substrates being permanently fabricated onto the archwire. In some implementations, each of the plurality of carbon-nanotube bonding substrates that is permanently fabricated to the archwire includes each of the plurality of carbon-nanotube bonding substrates being permanently fabricated into the archwire. In some aspects, the archwire includes no other apparatus.

In some aspects, an apparatus consists essentially of an archwire, and a plurality of carbon-nanotube bonding substrates each of the plurality of carbon-nanotube bonding substrates is permanently fabricated into the archwire at fixed positions of the archwire. In some implementations, each of the plurality of carbon-nanotube bonding substrates that is permanently fabricated into the archwire includes at least one of the plurality of carbon-nanotube bonding substrates that are formed as one complete integral unit with the archwire. In some implementations, each of the plurality of carbon-nanotube bonding substrates that is permanently fabricated into the archwire includes at least one of the plurality of carbon-nanotube bonding substrates are permanently fabricated to the archwire through a welding/brazing method that is appropriate for the materials of the archwire and the carbon-nanotube bonding substrate. In some implementations, each of the plurality of carbon-nanotube bonding substrates that is permanently fabricated into the archwire includes at least one of the plurality of carbon-nanotube bonding substrates being weldeded to the archwire. In some implementations, each of the plurality of carbon-nanotube bonding substrates that is permanently fabricated into the archwire at fixed positions of the archwire includes at least one of the plurality of carbon-nanotube bonding substrates are metallurgically permanently fabricated into the archwire at fixed positions of the archwire. In some implementations, each of the plurality of carbon-nanotube bonding substrates that is permanently fabricated into the archwire at fixed positions of the archwire includes at least one of the plurality of carbon-nanotube bonding substrates are glued onto the archwire at fixed positions of the archwire. In some implementations, the plurality of carbon-nanotube bonding substrates are 14 carbon-nanotube bonding substrates. In some implementations, each of the carbon-nanotube bonding substrates have an orientation to the archwire such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In some implementations, the orientation of each of the carbon-nanotube bonding substrates include providing the carbon-nanotube bonding substrates are accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the carbon-nanotube bonding substrates onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, each of the carbon-nanotube bonding substrates include at least one contour of each of the carbon-nanotube bonding substrates is produced from existing statistical norms of the labial and buccal surfaces of human teeth. In some implementations, each of the carbon-nanotube bonding substrates include an occlusal-gingival height in a range of 1.5 mm to 4 mm and a mesial-distal length in a range of 1.5 mm to 3.0 mm. In some implementations, the archwire includes thermally activated nickel-titanium (NiTi) metal, with force activation occurring at approximately 27 degrees Celsius and approximately 81 degrees Fahrenheit. In some implementations, the archwire includes a diameter selected from the group of diameters consisting of 0.012 inches in diameter round, 0.014 inches in diameter round, 0.016 round, and 0.016×0.0016 inches rectangular cross section. In some implementations, the archwire includes a tooth-color as a result of manufacturing with epoxy coatings or other tooth-colored surfaces. In some implementations, the at least one of the plurality of carbon-nanotube bonding substrates includes a tooth-color as a result of manufacturing with epoxy coatings or other tooth-colored surfaces. In some implementations, each of the plurality of carbon-nanotube bonding substrates that is permanently fabricated to the archwire includes each of the plurality of carbon-nanotube bonding substrates being permanently fabricated onto the archwire. In some implementations, each of the plurality of carbon-nanotube bonding substrates that is permanently fabricated to the archwire includes each of the plurality of carbon-nanotube bonding substrates being permanently fabricated into the archwire.

In some aspects, an apparatus includes an archwire, and a plurality of carbon-nanotube bonding substrates each of the plurality of carbon-nanotube bonding substrates is permanently fabricated to the archwire at fixed positions of the archwire. In some implementations, each of the plurality of carbon-nanotube bonding substrates that is permanently fabricated into the archwire includes each of the plurality of carbon-nanotube bonding substrates is formed as one complete integral unit with the archwire. In some implementations, each of the plurality of carbon-nanotube bonding substrates that is permanently fabricated into the archwire includes each of the plurality of carbon-nanotube bonding substrates is formed as one complete integral unit with the archwire. In some implementations, each of the plurality of carbon-nanotube bonding substrates that is permanently fabricated into the archwire includes each of the plurality of carbon-nanotube bonding substrates being permanently fabricated to the archwire through a welding/brazing method that is appropriate for the materials of the archwire and the carbon-nanotube bonding substrate. In some implementations, each of the plurality of carbon-nanotube bonding substrates that is permanently fabricated into the archwire includes each of the plurality of carbon-nanotube bonding substrates being welded to the archwire. In some implementations, the apparatus includes not having an orthodontic bracket. In some implementations, each of the plurality of carbon-nanotube bonding substrates that is permanently fabricated into the archwire at fixed positions of the archwire includes each of the plurality of carbon-nanotube bonding substrates being metallurgically permanently fabricated into the archwire at fixed positions of the archwire. In some implementations, each of the plurality of carbon-nanotube bonding substrates that is permanently fabricated into the archwire at fixed positions of the archwire includes each of the plurality of carbon-nanotube bonding substrates being glued onto the archwire at fixed positions of the archwire. In some implementations, the plurality of carbon-nanotube bonding substrates are 14 carbon-nanotube bonding substrates. In some implementations, each of the carbon-nanotube bonding substrates have an orientation to the archwire such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In some implementations, the orientation of each of the carbon-nanotube bonding substrates include providing the carbon-nanotube bonding substrates are accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the carbon-nanotube bonding substrates onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, each of the carbon-nanotube bonding substrates include at least one contour of each of the carbon-nanotube bonding substrates is produced from existing statistical norms of the labial and buccal surfaces of human teeth. In some implementations, each of the carbon-nanotube bonding substrates include an occlusal-gingival height in a range of 1.5 mm to 4 mm and a mesial-distal length in a range of 1.5 mm to 3.0 mm. In some implementations, the archwire includes thermally activated nickel-titanium (NiTi) metal. In some implementations, the thermally activated nickel-titanium (NiTi) metal includes force activation occurring at a temperature of approximately 27 degrees Celsius. In some implementations, the archwire includes a diameter selected from the group of diameters consisting of 0.012 inches in diameter round, 0.014 inches in diameter round, 0.016 inches in diameter round, and 0.016×0.016 rectangular cross section. In some implementations, the archwire includes a tooth-color as a result of manufacturing with epoxy coatings or other tooth-colored surfaces. In some implementations, the at least one of the plurality of carbon-nanotube bonding substrates includes a tooth-color as a result of manufacturing with epoxy coatings or other tooth-colored surfaces. In some implementations, each of the plurality of carbon-nanotube bonding substrates that is permanently fabricated to the archwire includes each of the plurality of carbon-nanotube bonding substrates being permanently fabricated onto the archwire. In some implementations, each of the plurality of carbon-nanotube bonding substrates that is permanently fabricated to the archwire includes each of the plurality of carbon-nanotube bonding substrates being permanently fabricated into the archwire.

In some aspects, an apparatus consists of an archwire, and at least one carbon-nanotube bonding substrate directly attached to the archwire. In some implementations, the at least one carbon-nanotube bonding substrate directly attached to the archwire includes the at least one carbon-nanotube bonding substrate is formed as one complete integral unit with the archwire. In some implementations, the at least one carbon-nanotube bonding substrate directly attached to the archwire includes the at least one carbon-nanotube bonding substrate is attached directly to the archwire through welding/brazing. In some implementations, the at least one carbon-nanotube bonding substrate directly attached to the archwire includes the at least one carbon-nanotube bonding substrate is welded to the archwire. In some implementations, the at least one carbon-nanotube bonding substrate directly attached to the archwire includes the at least one carbon-nanotube bonding substrate is metallurgically permanently fabricated into the archwire at fixed positions of the archwire. In some implementations, the at least one carbon-nanotube bonding substrate directly attached to the archwire includes the at least one carbon-nanotube bonding substrate is glued onto the archwire at fixed positions of the archwire. In some implementations, the at least one carbon-nanotube bonding substrate includes 14 carbon-nanotube bonding substrates. In some implementations, the at least one carbon-nanotube bonding substrate includes an orientation of the at least one carbon-nanotube bonding substrate to the archwire is such that when the at least one carbon-nanotube bonding substrate is applied to human teeth that are in orthodontically correct positions in all three planes of space, contours of exterior surfaces of the at least one carbon-nanotube bonding substrate are accurately appositioned with the occlusal-gingival center and the mesial-distal center of the labial and buccal contours of the human teeth. In some implementations, the orientation of the at least one carbon-nanotube bonding substrate includes providing the at least one carbon-nanotube bonding substrate is accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the at least one carbon-nanotube bonding substrate onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, the at least one carbon-nanotube bonding substrate includes at least one contour of the at least one carbon-nanotube bonding substrate is produced from existing statistical norms of the labial and buccal surfaces of human teeth. In some implementations, the at least one carbon-nanotube bonding substrate includes an occlusal-gingival height in a range of 1.5 mm to 4 mm and a mesial-distal length in a range of 1.5 mm to 3.0 mm. In some implementations, the at least one carbon-nanotube bonding substrate includes a tooth-color as a result of manufacturing with epoxy coatings or other tooth-colored surfaces. In some implementations, the archwire includes thermally activated nickel-titanium (NiTi) metal. In some implementations, the thermally activated nickel-titanium (NiTi) metal includes force activation occurring at a temperature of approximately 27 degrees Celsius. In some implementations, the archwire includes a diameter selected from the group of diameters consisting of 0.012 round, 0.014 inches in diameter round, 0.016 inches in diameter round, and 0.016×0.016 inches rectangular cross section. In some implementations, the archwire includes a tooth-color as a result of manufacturing with epoxy coatings or other tooth-colored surfaces.

In some aspects, an apparatus consists essentially of an archwire, and at least one carbon-nanotube bonding substrate directly attached to the archwire. In some implementations, the at least one carbon-nanotube bonding substrate directly attached to the archwire includes the at least one carbon-nanotube bonding substrate is formed as one complete integral unit with the archwire. In some implementations, the at least one carbon-nanotube bonding substrate directly attached to the archwire includes the at least one carbon-nanotube bonding substrate is directly attached to the archwire through a welding/brazing method that is appropriate for the materials of the archwire and the carbon-nanotube bonding substrate. In some implementations, the at least one carbon-nanotube bonding substrate directly attached to the archwire includes the at least one carbon-nanotube bonding substrate is welded to the archwire. In some implementations, the at least one carbon-nanotube bonding substrate directly attached to the archwire includes the at least one carbon-nanotube bonding substrate is metallurgically permanently fabricated into the archwire at fixed positions of the archwire. In some implementations, the at least one carbon-nanotube bonding substrate directly attached to the archwire includes the at least one carbon-nanotube bonding substrate is glued onto the archwire at fixed positions of the archwire. In some implementations, the at least one carbon-nanotube bonding substrate includes 14 carbon-nanotube bonding substrates. In some implementations, the at least one carbon-nanotube bonding substrate includes an orientation of the at least one carbon-nanotube bonding substrate to the archwire is such that when the at least one carbon-nanotube bonding substrate is applied to human teeth that are in orthodontically correct positions in all three planes of space, contours of exterior surfaces of the at least one carbon-nanotube bonding substrate are accurately appositioned with the occlusal-gingival center and the mesial-distal center of the labial and buccal contours of human teeth. In some implementations, the orientation of the at least one carbon-nanotube bonding substrate includes providing the at least one carbon-nanotube bonding substrate is accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the at least one carbon-nanotube bonding substrate onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, the at least one carbon-nanotube bonding substrate includes at least one contour of the at least one carbon-nanotube bonding substrate is produced from existing statistical norms of the labial and buccal surfaces of human teeth. In some implementations, the at least one carbon-nanotube bonding substrate includes an occlusal-gingival height in a range of 1.5 mm to 4 mm and a mesial-distal length in a range of 1.5 mm to 3.0 mm. In some implementations, the archwire includes thermally activated nickel-titanium (NiTi) metal, with force activation occurring at approximately 27 degrees Celsius and approximately 81 degrees Fahrenheit. In some implementations, the archwire includes a diameter selected from the group of diameters consisting of 0.012 inches in diameter round, 0.014 inches in diameter round, 0.016 inches in diameter round, and 0.016×0.016 rectangular cross section. In some implementations, the archwire includes a tooth-color as a result of manufacturing with epoxy coatings or other tooth-colored surfaces. In some implementations, the at least one carbon-nanotube bonding substrate includes a tooth-color as a result of manufacturing with epoxy coatings or other tooth-colored surfaces.

In some aspects, an apparatus includes an archwire, and at least one carbon-nanotube bonding substrate directly attached to the archwire. In some implementations, the at least one carbon-nanotube bonding substrate directly attached to the archwire includes the at least one carbon-nanotube bonding substrate is formed as one complete integral unit with the archwire. In some implementations, the at least one carbon-nanotube bonding substrate directly attached to the archwire includes the at least one carbon-nanotube bonding substrate is formed as one complete integral unit with the archwire. In some implementations, the at least one carbon-nanotube bonding substrate directly attached to the archwire includes the at least one carbon-nanotube bonding substrate is permanently fabricated to the archwire through a welding/brazing method that is appropriate for the materials of the archwire and the carbon-nanotube bonding substrate. In some implementations, the at least one carbon-nanotube bonding substrate directly attached to the archwire includes the at least one carbon-nanotube bonding substrate is welded to the archwire. In some implementations, the apparatus includes not having an orthodontic bracket. In some implementations, the at least one carbon-nanotube bonding substrate directly attached to the archwire includes the at least one carbon-nanotube bonding substrate is metallurgically permanently fabricated into the archwire at fixed positions of the archwire. In some implementations, the at least one carbon-nanotube bonding substrate directly attached to the archwire includes the at least one carbon-nanotube bonding substrate is glued onto the archwire at fixed positions of the archwire. In some implementations, the at least one carbon-nanotube bonding substrate includes 14 carbon-nanotube bonding substrates. In some implementations, the at least one carbon-nanotube bonding substrate includes an orientation of the at least one carbon-nanotube bonding substrate to the archwire is such that when the at least one carbon-nanotube bonding substrate is applied to human teeth that are in orthodontically correct positions in all three planes of space, contours of exterior surfaces of the at least one carbon-nanotube bonding substrate are accurately appositioned with the occlusal-gingival center and the mesial-distal center of the labial and buccal contours of the human teeth. In some implementations, the orientation of the at least one carbon-nanotube bonding substrate includes providing the at least one carbon-nanotube bonding substrate is accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations the apparatus is produced by a method including setting typodont teeth in orthodontically correct positions; placing the at least one carbon-nanotube bonding substrate onto the typodont teeth in the occlusal-gingival center and mesial-distal center of the labial and buccal aspect of orthodontically correct positions; and attaching the archwire in a horizontal plane, to an exterior surface of each of the plurality of carbon-nanotube bonding substrates. In some implementations, the at least one carbon-nanotube bonding substrate includes at least one contour of the at least one carbon-nanotube bonding substrate is produced from existing statistical norms of the labial and buccal surfaces of human teeth. In some implementations, the at least one carbon-nanotube bonding substrate includes an occlusal-gingival height in a range of 1.5 mm to 4 mm and a mesial-distal length in a range of 1.5 mm to 3.0 mm. In some implementations, the at least one carbon-nanotube bonding substrate includes a tooth-color as a result of manufacturing with epoxy coatings or other tooth-colored surfaces. In some implementations, the archwire includes thermally activated nickel-titanium (NiTi) metal. In some implementations, the thermally activated nickel-titanium (NiTi) metal includes force activation occurring at a temperature of approximately 27 degrees Celsius. In some implementations, the archwire includes a diameter selected from the group of diameters consisting of 0.012 inches in diameter round, 0.014 inches in diameter round, 0.016 inches in diameter round, and 0.016×0.016 inches rectangular cross section. In some implementations, the archwire includes a tooth-color as a result of manufacturing with epoxy coatings or other tooth-colored surfaces.

In some aspects, a method includes setting typodont teeth in orthodontically correct positions, placing a plurality of carbon-nanotube bonding substrates onto the typodont teeth in the occlusal-gingival center and mesial-distal center of the labial and buccal aspect of orthodontically correct positions, and attaching permanently an archwire to the exterior surface of each of the plurality of the carbon-nanotube bonding substrates in a plane. In some implementations, the method includes not attaching an orthodontic bracket. In some implementations, the method includes attaching permanently the archwire to the exterior surface of each of the plurality of the carbon-nanotube bonding substrates includes forming the archwire as one complete integral unit with the plurality of carbon-nanotube bonding substrates. In some implementations, the method includes attaching permanently the archwire to the exterior surface of each of the plurality of the carbon-nanotube bonding substrates includes welding/brazing the archwire to the exterior surface of each of the plurality of the carbon-nanotube bonding substrates In some implementations, the method includes attaching permanently the archwire to the exterior surface of each of the plurality of the carbon-nanotube bonding substrates includes welding each of the plurality of carbon-nanotube bonding substrates to the archwire. In some implementations, the method includes attaching permanently the archwire to the exterior surface of each of the plurality of the carbon-nanotube bonding substrates includes fabricating metallurgically the archwire into each of the plurality of carbon-nanotube bonding substrates. In some implementations, the method includes attaching permanently the archwire to the exterior surface of each of the plurality of the carbon-nanotube bonding substrates includes gluing the archwire to each of the plurality of carbon-nanotube bonding substrates. In some implementations, the method includes the plurality of carbon-nanotube bonding substrates includes 14 carbon-nanotube bonding substrates. In some implementations, the method includes an orientation of each of the carbon-nanotube bonding substrates to the archwire such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In some implementations, the method includes the orientation of each of the carbon-nanotube bonding substrates include providing the carbon-nanotube bonding substrates as accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations, the method includes producing at least one contour of each of the carbon-nanotube bonding substrates based on existing statistical norms of the labial and buccal surfaces of human teeth. In some implementations, the method includes each of the carbon-nanotube bonding substrates include an occlusal-gingival height in a range of 1.5 mm to 4 mm and a mesial-distal length in a range of 1.5 mm to 3.0 mm. In some implementations, the method includes the archwire includes thermally activated nickel-titanium (NiTi) metal. In some implementations, the thermally activated nickel-titanium (NiTi) metal includes force activation occurring at a temperature of approximately 27 degrees Celsius. In some implementations, the method includes the archwire includes a diameter selected from the group of diameters consisting of 0.012 inches in diameter round, 0.014 inches in diameter round, 0.016 inches in diameter round, and 0.016×0.016 inches rectangular cross section. In some implementations, the method includes the archwire includes a tooth-color as a result of manufacturing with epoxy coatings or other tooth-colored surfaces. In some implementations, the method includes the at least one of the plurality of carbon-nanotube bonding substrates includes a tooth-color as a result of manufacturing with epoxy coatings or other tooth-colored surfaces.

In some aspects, a method includes setting typodont teeth in orthodontically correct positions, placing a plurality of carbon-nanotube bonding substrates onto the typodont teeth in the occlusal-gingival center and mesial-distal center of the labial and buccal aspect of orthodontically correct positions, and forming an archwire to an exterior surface of each of the plurality of the carbon-nanotube bonding substrates in a horizontal plane. In some implementations, the method includes not attaching an orthodontic bracket. In some implementations, the method includes forming an archwire to an exterior surface of each of the plurality of the carbon-nanotube bonding substrates includes forming the archwire as one complete integral unit with the plurality of carbon-nanotube bonding substrates. In some implementations, the method includes forming an archwire to an exterior surface of each of the plurality of the carbon-nanotube bonding substrates includes welding/brazing the archwire to the exterior surface of each of the plurality of the carbon-nanotube bonding substrates In some implementations, the method includes forming an archwire to an exterior surface of each of the plurality of the carbon-nanotube bonding substrates includes welding each of the plurality of carbon-nanotube bonding substrates to the archwire. In some implementations, the method includes forming an archwire to an exterior surface of each of the plurality of the carbon-nanotube bonding substrates includes fabricating metallurgically the archwire into each of the plurality of carbon-nanotube bonding substrates. In some implementations, the method includes forming an archwire to an exterior surface of each of the plurality of the carbon-nanotube bonding substrates includes gluing the archwire to each of the plurality of carbon-nanotube bonding substrates. In some implementations of the method the plurality of carbon-nanotube bonding substrates includes 14 carbon-nanotube bonding substrates. In some implementations of the method includes an orientation of each of the carbon-nanotube bonding substrates to the archwire such that when the carbon-nanotube bonding substrates are applied to human teeth that are in orthodontically correct positions in all three planes of space, contours of exterior surfaces of the carbon-nanotube bonding substrates are accurately appositioned with the occlusal-gingival center and the mesial-distal center of the labial and buccal contours of the human teeth. In some implementations of the method includes providing the carbon-nanotube bonding substrates as accurately appositioned with labial and buccal aspects at occlusal-gingival center and mesial-distal center to the extent that human teeth that are not in orthodontically correct positions will experience corrective orthodontic forces moving the human teeth toward orthodontically correct positions. In some implementations, the method includes producing at least one contour of each of the carbon-nanotube bonding substrates based on existing statistical norms of the labial and buccal surfaces of human teeth. In some implementations of the method, each of the carbon-nanotube bonding substrates include an occlusal-gingival height in a range of 1.5 mm to 4 mm and a mesial-distal length in a range of 1.5 mm to 3.0 mm. In some implementations of the method the archwire includes a thermally activated nickel-titanium (NiTi) metal, with force activation occurring at approximately 27 degrees Celsius and approximately 81 degrees Fahrenheit. In some implementations of the method the archwire includes a diameter selected from the group of diameters consisting of 0.012 inches in diameter round, 0.014 inches in diameter round, 0.016 inches in diameter round, and 0.016×0.016 inches rectangular cross section. In some implementations of the method the archwire includes a tooth-color as a result of manufacturing with epoxy coatings or other tooth-colored surfaces. In some implementations of the method the at least one of the plurality of carbon-nanotube bonding substrates includes a tooth-color as a result of manufacturing with epoxy coatings or other tooth-colored surfaces.

In some implementations, apparatus that consists of the archwire and the plurality of carbon-nanotube bonding substrates include only the major components the archwire and the plurality of carbon-nanotube bonding substrates. An attachment apparatus is not a major component of the apparatus but merely provides a manner of attaching the archwire to the plurality of carbon-nanotube bonding substrates without a major structural component in between the archwire and the plurality of carbon-nanotube bonding substrates.

In some implementations, apparatus that consists essentially of the archwire and the plurality of carbon-nanotube bonding substrates excludes additional limitations that materially affect the basic characteristic of the archwire and the plurality of carbon-nanotube bonding substrates. An attachment apparatus is not a major component of the apparatus but merely provides a manner of attaching the archwire to the plurality of carbon-nanotube bonding substrates without a major structural component in between the archwire and the plurality of carbon-nanotube bonding substrates.

In some of the implementations of permanent attachment, the permanent attachment is a semi-permanent attachment, such as a removeable attachment.

The invention claimed is:

1. An orthodontic bracket comprising:
   a tooth bonding pad including:
      a bracket bonding surface having a flat surface;
      a carbon-nanotube bonding substrate directly attached to the flat surface of the bracket bonding surface; and
      a forest of carbon-nanotubes that is attached to the carbon-nanotube bonding substrate;
   at least one tie wing attached to the tooth bonding pad,
   wherein the carbon-nanotube bonding substrate further comprises a silicone dioxide growth substrate,
   wherein the forest of the carbon-nanotubes provides that the bracket bonding surface having the flat surface on the orthodontic bracket to adhere to a tooth enamel through Van der Wall intermolecular forces between the forest of the carbon-nanotubes and the tooth enamel;
   wherein the forest of the carbon-nanotubes allows installation and removal of the orthodontic bracket from the tooth enamel without dental cement.

\* \* \* \* \*